(12) United States Patent
Song et al.

(10) Patent No.: US 11,129,597 B2
(45) Date of Patent: Sep. 28, 2021

(54) ADAPTIVE MEDICAL IMAGE TRANSMISSION DEVICE AND METHOD

(71) Applicant: SOGANG UNIVERSITY RESEARCH FOUNDATION, Seoul (KR)

(72) Inventors: Tai-Kyong Song, Seoul (KR); Woo Kyu Kong, Seoul (KR); Sun Mi Yeo, Gyeongsangbuk-do (KR); Gi-Duck Kim, Seoul (KR); Jaejin Lee, Seoul (KR); Jeeun Kang, Seoul (KR); Jong Ho Park, Incheon (KR); Yeongnam Lee, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 712 days.

(21) Appl. No.: 15/737,478

(22) PCT Filed: Jun. 18, 2015

(86) PCT No.: PCT/KR2015/006217
§ 371 (c)(1),
(2) Date: Dec. 18, 2017

(87) PCT Pub. No.: WO2016/204326
PCT Pub. Date: Dec. 22, 2016

(65) Prior Publication Data
US 2018/0168554 A1 Jun. 21, 2018

(51) Int. Cl.
A61B 8/00 (2006.01)
H04W 52/02 (2009.01)
(Continued)

(52) U.S. Cl.
CPC .............. *A61B 8/56* (2013.01); *A61B 8/4427* (2013.01); *A61B 8/4472* (2013.01); *A61B 8/462* (2013.01);
(Continued)

(58) Field of Classification Search
CPC ....... H04L 47/25; H04L 47/38; H04L 1/0014; H04L 1/0001; H04W 28/06;
(Continued)

(56) References Cited

U.S. PATENT DOCUMENTS

2003/0017846 A1* 1/2003 Estevez ................ H04N 19/154
455/556.1
2005/0114395 A1 5/2005 Muralidharan
(Continued)

FOREIGN PATENT DOCUMENTS

JP 08-221557 8/1996
JP 2000-157518 6/2000
(Continued)

*Primary Examiner* — Bo Joseph Peng
(74) *Attorney, Agent, or Firm* — Duane Morris LLP; Gregory M. Lefkowitz; Joaquin Hernandez

(57) ABSTRACT

The present invention relates to an adaptive medical image transmission device and method which consider communication state and residual power. The adaptive medical image transmission method induces an image receiving device to post-process a result of medical image processing performed by a medical image transmission device by: receiving medical image data by means of a probe; sensing communication throughput indicative of a communication state between the image transmission device and the image receiving device; variably determining a data rate required to transmit data on the basis of a preset data rate based on the sensed communication throughput; performing medical image processing by selecting a signal path which satisfies the determined data rate with respect to the medical image data; and transmitting (Continued)

the result of the medical image processing to the image receiving device according to the determined data rate.

6 Claims, 12 Drawing Sheets

(51) Int. Cl.
| | |
|---|---|
| *H04W 28/06* | (2009.01) |
| *H04L 1/00* | (2006.01) |
| *A61B 8/08* | (2006.01) |
| *H04W 52/00* | (2009.01) |
| *H04N 19/10* | (2014.01) |
| *H04W 28/00* | (2009.01) |
| *A61B 8/14* | (2006.01) |

(52) U.S. Cl.
CPC .......... *A61B 8/5215* (2013.01); *H04L 1/0014* (2013.01); *H04W 28/06* (2013.01); *H04W 52/0261* (2013.01); *A61B 8/14* (2013.01); *H04L 1/0001* (2013.01); *H04N 19/10* (2014.11); *H04W 28/00* (2013.01); *H04W 52/00* (2013.01)

(58) Field of Classification Search
CPC . H04W 52/0261; H04W 52/00; H04W 28/00; H05N 19/10; G01S 7/5208; G01S 7/52085; G01S 15/8915; G01S 7/52034; G01S 7/52033; A61B 8/5215; A61B 8/4472; A61B 8/4427; A61B 8/56; A61B 8/4494; A61B 8/5207; A61B 8/488; A61B 8/4483

See application file for complete search history.

(56) References Cited

U.S. PATENT DOCUMENTS

2014/0164596 A1    6/2014  Hoctor et al.
2015/0297193 A1*  10/2015  Rothberg ................. A61B 8/56
                                                            600/459

FOREIGN PATENT DOCUMENTS

| JP | 2013-094341 | 5/2013 |
| KR | 10-2007-0054820 | 8/2007 |
| KR | 10-2012-0091209 | 8/2012 |

* cited by examiner

ADAPTIVE MEDICAL IMAGE TRANSMISSION DEVICE AND METHOD

CROSS-REFERENCE TO RELATED APPLICATIONS

This application is a § 371 national stage entry of International Application No. PCT/KR2015/006217, filed on Jun. 18, 2015, the entire contents of which are incorporated herein by reference.

TECHNICAL FIELD

The present invention relates to techniques of transmitting and receiving a medical image and, particularly, to a device and a method for transmitting a medical image between a transmitting end and a receiving end in a portable wireless ultrasound imaging system in which a medical imaging device at a transmitting side which is connected to a probe in proximity to a to-be-measured object and a medical image reception device at a receiving side are physically separated from each other, and a recording medium in which the method is recorded.

BACKGROUND ART

Medical imaging technology is a diagnosis technique of visually representing muscles, tendons, and many internal organs, to capture their size, structure, and pathologic lesions with real-time tomographic images, based on an ultrasound or photoacoustic means. Medical imaging is also used to visualize fetuses during a periodic checkup or in an emergency situation. Ultrasound has been used to image the interior of the human body for at least 50 years and has become one of the most widely used diagnostic tools in modern medicine. The ultrasound technique is low in cost and highly portable, relative to magnetic resonance imaging (MRI) or X-ray computed tomography (CT).

The principle of ultrasound imaging is as follows. First, an ultrasound image is made by bringing a measurement object into contact with a probe and receiving ultrasound reflected by generation of ultrasound waves. If ultrasound is generated, an ultrasound wave passes into a medium within a very short time and the ultrasound wave is reflected upon passing between two media having different acoustic impedances. In the ultrasound imaging technique, such a reflection wave is measured and a distance is calculated based on the time until reflection sound returns back, thereby achieving imaging.

Various ultrasound medical imaging techniques have been proposed using the advantages of real-time and nondestructive/noninvasive imaging of ultrasound images. In particular, ultrasound medical imaging systems which were realized as large equipment tend to be developed as smaller portable equipment, and Korean Patent Publication No. 10-2008-0046888 (published on May 28, 2008, Medicine company), a prior art document, proposes a general idea for a portable ultrasound system.

DETAILED DESCRIPTION OF THE INVENTION

Technical Problems

The technical objects that can be achieved through the present invention are designed to solve problems that equipment of a transmitting end and equipment of a receiving end process images in a fixed manner in portable ultrasound medical equipment proposed in order to overcome the limitations of conventional integral ultrasound medical equipment which is difficult to carry and thus cannot cope with changes in a communication environment between the transmitting end and the receiving end, to overcome the limitations that malfunction of an ultrasound medical imaging system occurs when any one of transmitting end equipment and receiving end equipment, which are physically separated from each other exhausts residual power, and to resolve the demerits that user experience is deteriorated because remote medical imaging systems remain in a state of compressing image data according to a fixed rule without considering situations and environments in which a communication state is restricted and important medical information that must be maintained with high image quality is lost.

Technical Solutions

To accomplish the technical objects, a medical image transmission method performed by an image transmission device according to an embodiment of the present invention includes: receiving medical image data using a probe; detecting communication throughput indicating a communication state between the image transmission device and an image reception device; variably determining a data rate necessary for data transmission on the basis of a preset data rate based on the communication throughput; performing medical image processing by selecting a signal path satisfying the determined data rate with respect to the medical image data; and transmitting the result of the medical image processing to the image reception device according to the determined data rate to induce the image reception device to post-process the result of the medical image processing performed by the image transmission device.

In the medical image transmission method performed by an image transmission device according to an embodiment, upon detecting that the communication throughput decreases below a threshold value due to a communication state variation, the image transmission device may control a decimation ratio to be inversely proportional to the detected communication throughput and control the number of scanlines to be proportional to the detected communication throughput to induce the result of the medical image processing to satisfy a preset frame rate and image quality.

In the medical image transmission method performed by an image transmission device according to an embodiment, the preset frame rate and image quality may be respectively assigned weights according to user selection, the image transmission device may increase a rate of increase in the decimation ratio and a ratio of reduction in the number of scanlines and reduce the number of samples per length when a larger weight is assigned to the frame rate than the image quality, and the image transmission device may suppress a reduction in the number of samples per length while maintaining the ratio of increase in the decimation ratio and the rate of reduction in the number of scanlines when a larger weight is assigned to the image quality than the frame rate.

To accomplish the technical objects, a medical image reception method performed by an image reception device according to another embodiment of the present invention includes: receiving a result of medical image processing from an image transmission device; analyzing the result of the medical image processing to identify a pre-processing procedure; and post-processing the result of the medical image processing subsequently to the identified pre-processing procedure, wherein the pre-processing procedure is a procedure performed by the image transmission device by receiving medical image data using a probe, detecting communication throughput indicating a communication state between the image transmission device and the image reception device, variably determining a data rate necessary for data transmission on the basis of a preset data rate based on the communication throughput and selecting a signal path satisfying the determined data rate with respect to the medical image data.

To accomplish the technical objects, a medical image transmission method performed by a remote medical imaging system according to another embodiment of the present invention includes: generating a medical image using a probe; setting a region of interest (ROI) in the generated medical image and segmenting the medical image into one or more regions depending on distance from the set ROI; applying a differential image data reduction technique to the segmented regions to generate reduced image data per segmented region; and transmitting the reduced image data to a local medical imaging system.

In the medical image transmission method performed by a remote medical imaging system according to another embodiment, the generating of the reduced image data may include applying different image data reduction techniques to the segmented regions such that segmented regions separated from the ROI have higher data compressibility than the ROI.

To accomplish the technical objects, a medical image reception method performed by a local medical imaging system according to another embodiment of the present invention includes: receiving a medical image from a remote medical imaging system; analyzing the received medical image to reconstruct reduced image data per segmented region; and outputting the reconstructed image data, wherein the reduced image data is generated by the remote medical imaging system by generating a medical image using a probe, setting an ROI in the generated medical image, segmenting the medical image into one or more regions depending on distance from the set ROI, and applying a differential image data reduction technique to the segmented regions.

To accomplish the technical objects, a medical image transmission method performed by an image transmission device according to another embodiment of the present invention includes: acquiring medical image data using a probe; evaluating at least one of a communication state and a power state between the image transmission device and an image reception device; determining a reconstruction parameter according to the evaluation result and reconstructing a first medical image from the medical image data according to the reconstruction parameter; encoding the reconstructed first medical image to generate compressed data; and transmitting the generated compressed data to the image reception device to induce the image reception device to generate a post-processed second medical image from the compressed data.

In the medical image transmission method performed by an image transmission device according to another embodiment, the reconstructing of the first medical image may include variably determining a reconstruction parameter for image reconstruction such that the size of the first medical image is proportional to throughput according to the communication state or residual power according to the power state.

To accomplish the technical objects, a medical image reception method performed by an image reception device according to another embodiment of the present invention includes: receiving compressed data from an image transmission device; decoding the received compressed data to reconstruct a first medical image; and post-processing the reconstructed first medical image to generate a second medical image, wherein the compressed data is generated by the image transmission device by acquiring medical image data using a probe, evaluating at least one of a communication state and a power state between the image transmission device and an image reception device, determining a reconstruction parameter according to the evaluation result, reconstructing the first medical image from the medical image data according to the reconstruction parameter and encoding the reconstructed first medical image.

Furthermore, a computer-readable recording medium storing a program which causes a computer to execute the aforementioned methods of transmitting a medical image and the aforementioned methods of receiving a medial image is provided.

Advantageous Effects

Embodiments of the present invention can adaptively change a data rate of data to be wirelessly transmitted by varying signal processing steps performed between a transmitting end and a receiving end according to communication conditions to provide ultrasound images at a uniform frame rate to a user irrespective of communication conditions and efficiently distribute use of batteries of the transmitting end and the receiving end to extend system available time.

In addition, embodiments of the present invention can maintain interest information obtained by the user while minimizing loss of important medical data in a wireless communication network with a limited bandwidth by segmenting a medical image acquired using a probe into regions, providing a specific region in which a user is interested with high image quality and decreasing image quality of other regions to minimize the amount of data to be wirelessly transmitted, and supplement an insufficient communication bandwidth by adopting a graded data reduction method to maximize user experience.

DESCRIPTION OF REFERENCE NUMERALS

Figure 1:
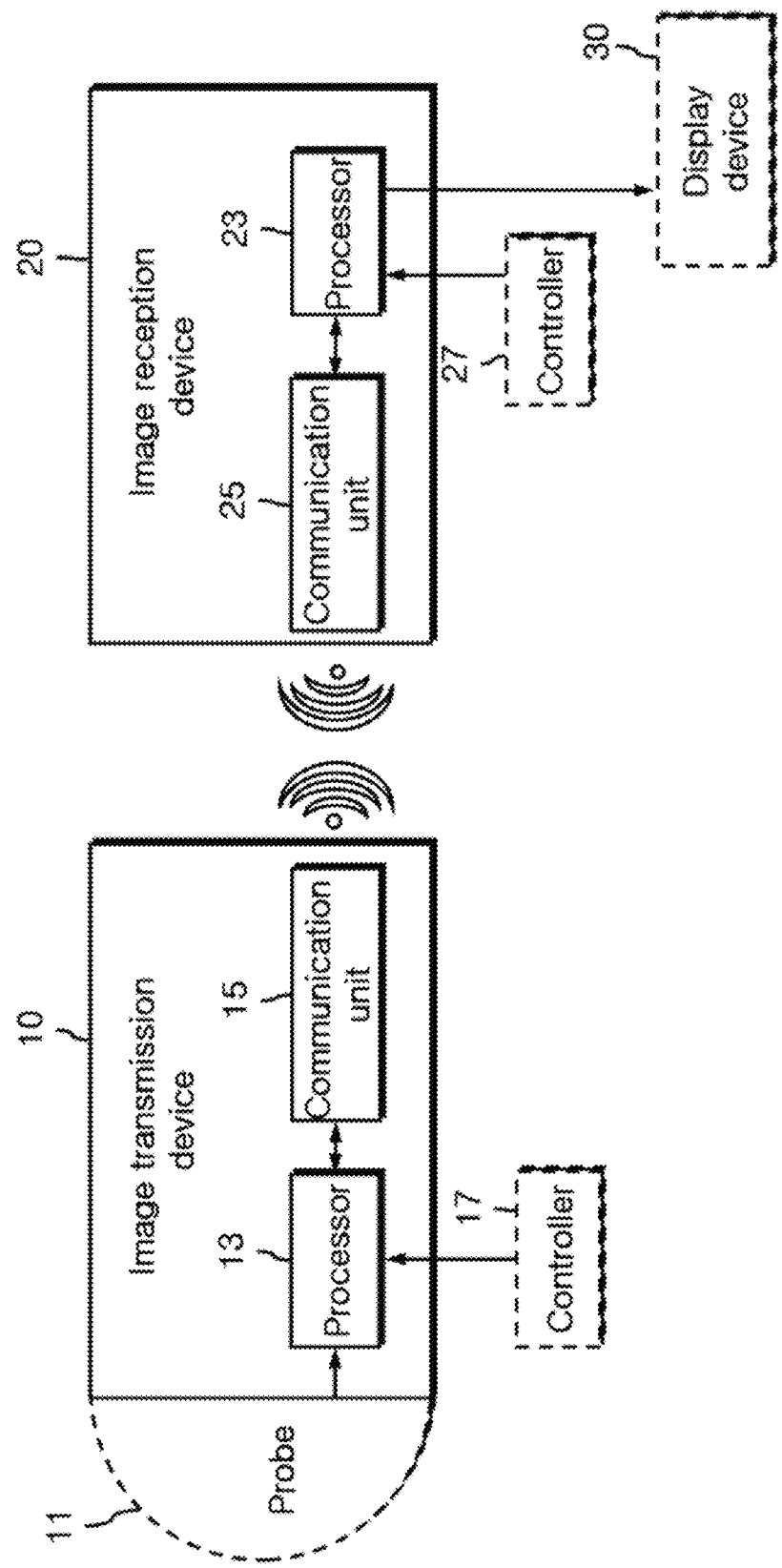
FIG. 1 is a block diagram illustrating the overall structure of a wireless ultrasound imaging system according to an embodiment of the present invention.

10: image transmission device/remote medical imaging device (transmitting end)
11: probe
13: image transmission device/processor of remote medical imaging device
15: image transmission device/communication unit of remote medical imaging device
17: image transmission device/controller of remote medical imaging device
20: image reception device/local medical imaging device (receiving end)
23: image reception device/processor of local medical imaging device (receiving end)
25: image reception device/communication unit of local medical imaging device (receiving end)
27: image reception device/controller of local medical imaging device (receiving end)
30: display device

BEST MODE FOR CARRYING OUT THE INVENTION

A method of transmitting a medical image by an image transmission device according to first embodiments of the present invention receives medical image data using a probe, detects communication throughput which indicates a communication state between the image transmission device and an image reception device, determines a data rate necessary for data transmission on the basis of a preset data rate based on the communication throughput, performs medical image processing by selecting a signal path satisfying the determined data rate with respect to the medical image data and transmits the result of the medical image processing to the image reception device according to the determined data rate.

A medical image transmission method performed by a remote medical imaging system according to second embodiments of the present invention generates a medical image using a probe, sets a region of interest (ROI) in the generated medical image, segments the medical image into one or more regions depending on distance from the set ROI, applies a differential image data reduction technique to the segmented regions to generate reduced image data per segmented region and transmits the reduced image data to a local medical imaging system.

A medical image transmission method performed by an image transmission device according to third embodiments of the present invention acquires medical image data using a probe, evaluates at least one of a communication state and a power state between the image transmission device and an image reception device, determines a reconstruction parameter according to the evaluation result and reconstructing a first medical image from the medical image data according to the reconstruction parameter, encodes the reconstructed first medical image to generate compressed data and transmits the generated compressed data to the image reception device to induce the image reception device to generate a post-processed second medical image from the compressed data.

MODE FOR INVENTION

Prior to a description of embodiments of the present invention, necessity and technical problems of a portable medical ultrasound imaging device will be briefly introduced and then technical means adopted by the embodiments of the present invention in order to solve these problems will be sequentially proposed.

Past medical ultrasound imaging systems were manufactured on a large scale and installed in medical facilities, and used for diagnosis of patients visiting hospitals. However, it is necessary to provide functional and anatomical medical images of patients in a situation in which patients cannot visit hospitals in emergency medical care and home medical care fields. Accordingly, a mobile ultrasound imaging system which can be mounted in ambulances and the like was developed but this system cannot be easily carried by a person.

(1) First Embodiments

The first embodiments of the present invention propose a portable medical ultrasound imaging system in which a probe capable of generating ultrasound waves and receiving ultrasound waves reflected from the human body is separately configured, the probe or a medical imaging device at a transmitting side connected to the probe performs part of ultrasound image processing and then transmits the result to a smartphone, a smart pad or a personal portable terminal corresponding to a receiving side through wired/wireless communication, and the receiving side performs the remaining image processing to obtain a final ultrasound image. Problems estimated in implementation of this portable medical ultrasound imaging system are as follows.

First, communication performance between a transmitting end including a probe or connected thereto and a receiving end needs to be considered. That is, the state of a communication medium connected between the transmitting end and the receiving end may vary, and particularly in the case of wireless communication, various faults may occur according to operation environments. Accordingly, it is necessary to determine operations performed by the transmitting end and the receiving end in consideration of a communication state. Such consideration of communication state necessarily leads to determination of the range of an image post-processing procedure that needs to be performed at the transmitting end, which will be described below with reference to the drawings.

Second, both of transmitting end equipment which includes a probe or is connected thereto and receiving end equipment are implemented as portable equipment, and thus power consumption thereof is limited. In addition, when there is a difference between residual power of the transmitting end equipment and residual power of the receiving end equipment, power shortage of one side may lead to malfunction of the ultrasound medical imaging system. Accordingly, it is necessary to determine operations performed by the transmitting end and the receiving end in consideration of physically separated batteries of both sides. This is also associated with determination of the range of the image post-processing procedure that needs to be performed by the transmitting end.

Therefore, embodiments of the present invention which will be described below propose technical means for reducing a data rate to improve a frame rate when communication conditions deteriorate in a portable medical ultrasound imaging system and extending system available time through efficient distribution of battery use. To this end, the embodiments of the present invention variably determine boundaries of signal processing blocks processed in the transmitting end and the receiving end in consideration of data rate changes according to communication environment in a portable wireless medical ultrasound imaging system including the receiving end that can perform wireless communication with a wireless probe included in the transmitting end or connected thereto and process image signals, to thereby provide, to a user, an image which satisfies a frame rate and image quality selected by the user even in the case of communication environment change. Furthermore, the embodiments of the present invention cause the receiving end and the transmitting end to interactively monitor battery gauges and efficiently distribute processed signals depending on the battery gauges to extend available time of a portable wireless ultrasound imaging system operating based on a battery.

Hereinbelow, first embodiments of the present invention will be described in detail with reference to the drawings. The same reference numerals represent the same components throughout the drawings.

FIG. 1 is a block diagram illustrating the overall structure of a wireless ultrasound imaging system according to embodiments of the present invention. The wireless ultrasound imaging system includes an image transmission device/remote medical imaging device 10 and an image reception device/local medical imaging device 20. Since FIG. 1 illustrates the structure covering other embodiments as well as the present embodiment, the configuration of the system will be described repeatedly for the embodiments on the basis of discriminative features. The image transmission device 10 may include a probe 11 which radiates a measurement signal to a measurement target and receives a response signal to the measurement signal or may be electrically connected thereto. A description of the detailed configuration of the probe 11 is omitted since the essence of the present invention may be obscured.

In embodiments which will be described below, a medical image will be described as an ultrasound image, but this is proposed as an example among various embodiments sharing the same technical idea and the medical image is not limited to ultrasound images. Furthermore, the image transmission device and the image reception device are connected using a wired or wireless communication means to transmit medical image processing results, and in the following embodiments, wireless communication is assumed for convenience.

In the image transmission device 10, a processor 13 receives medical image data using the probe 11. A communication unit 15 of the image transmission device 10 detects communication throughput indicating a communication state between the image transmission device 10 and the image reception device 20 and provides the detected communication throughput to the processor 13. Then, the processor 13 determines a data rate necessary for data transmission on the basis of a preset data rate based on the detected communication throughput. The processor 13 of the image transmission device 10 to perform medical image processing by selecting a signal path which satisfies the determined data rate with respect to medical image data. Such medical image processing corresponds to an image pre-processing procedure performed at the transmitting end. The image transmission device 10 transmits the result of medical image processing to the image reception device 20 according to the determined data rate through the communication unit 15. More specific procedures performed by the image transmission device 10 will be described below with reference to FIGS. 2 to 6.

The image reception device 20 receives the result of the medical image processing from the image transmission device 10 through a communication unit 25. Then, a processor 23 of the image reception device 20 analyzes the received medical image processing result to identify a pre-processing procedure. Here, the pre-processing procedure refers to an image processing procedure according to the signal path selected through the image transmission device 10. The processor 23 post-processes the medical image processing result received through the communication unit 25 subsequently to the identified pre-processing procedure. The post-processing procedure refers to a procedure other than the pre-processing procedure in the entire procedure for generating a final medical image signal from the original signal received through the probe 11. Finally, the processor 23 outputs a final medical image to a display device 30. More specific procedures performed by the image reception device 20 will be described below with reference to FIG. 7.

Figure 2:
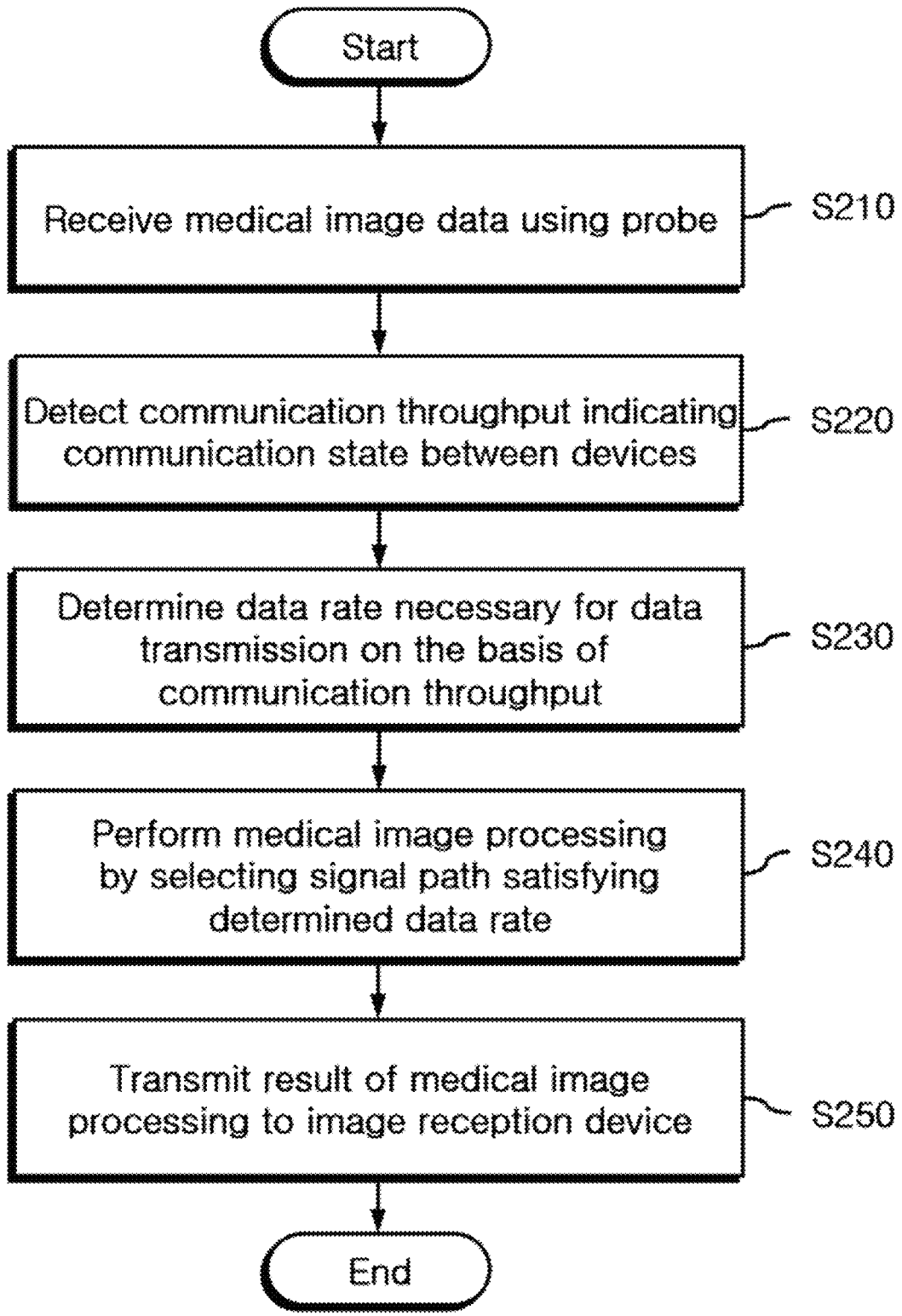
FIG. 2 is a flowchart illustrating a method of adaptively transmitting, by an image transmission device, a medical image according to selection of a signal path according to an embodiment of the present invention.

FIG. 2 is a flowchart illustrating a method of transmitting a medical image on the basis of the image transmission device according to an embodiment of the present invention.

In the wireless ultrasound imaging system, data is wirelessly transmitted from the transmitting end connected to the probe to the receiving end in charge of image signal processing. However, a wireless data transmission rate is variable according to surrounding communication environments. Accordingly, when communication conditions abruptly deteriorate, images at a uniform frame rate cannot be provided to a user. In addition, the system cannot be used when any one of the transmitting end and the receiving end has low battery power. The proposed technique varies signal processing blocks processed in the transmitting end and the receiving end according to communication conditions to guarantee a frame rate and picture quality set when the user initiates the system and induces any one of the transmitting end and the receiving end which has sufficient battery power to process a larger amount of signals using the fact that battery consumption is low when the quantity of operations is small, thereby extending available time of the wireless ultrasound imaging system operating with a battery.

In step S210, the image transmission device receives medical image data using the probe.

In step S220, the image transmission device detects communication throughput indicating a communication state between the image transmission device and the image reception device. The communication throughput may be detected using various communication channel detection techniques used in network technology fields, and communication state indexes proposed in wired or wireless communication specifications may be used.

In step S230, the image transmission device determines a data rate necessary for data transmission on the basis of a preset data rate based on the communication throughput detected in step S220. For example, if currently detected communication throughput is less than the preset data rate, it is desirable to reduce the data rate necessary for data transmission.

In step S240, the image transmission device performs medical image processing by selecting a signal path which satisfies the data rate determined in step S230 with respect to the medical image data received in step S2109. Here, the signal path means part of a series of operation procedures performed in order to generate an image signal in the ultrasound imaging system, which will be performed by the image transmission device, and will be described in detail below with reference to FIGS. 3 to 5.

In step S250, the image transmission device transmits the result of medical image processing performed in step S240 to the image reception device according to the data rate determined in step S230.

Figure 3:
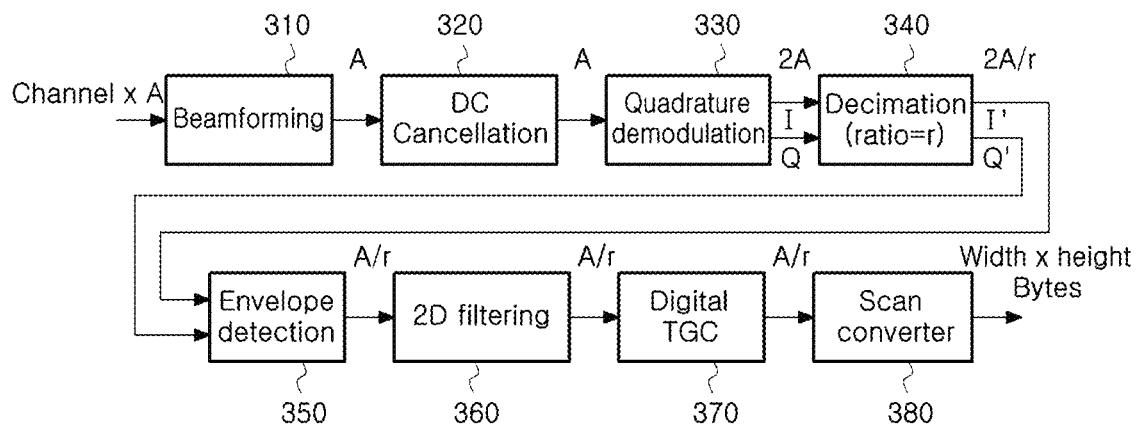
FIG. 3 is a block diagram illustrating a signal processing procedure of an ultrasound imaging system applied to embodiments of the present invention.

FIG. 3 is a block diagram illustrating a series of signal processing procedures of the ultrasound imaging system applied to embodiments of the present invention, which correspond to a signal path of a general ultrasound image processing system. Accordingly, detailed description of operations performed by each signal processing block is omitted so as not to obscure the subject matter of the present invention.

As discussed above with reference to FIG. 2, embodiments of the present invention are implemented using at least two devices of a transmitting end and a receiving end which are physically separated from each other to realize a portable ultrasound imaging system instead of being implemented using single hardware. Accordingly, it is necessary to determine a part of the signal path shown in FIG. 3, which will be processed by the transmitting end, and a part thereof which will be processed by the receiving end. In such determination, the embodiments of the present invention consider communication conditions between the transmitting end and the receiving end and the residual battery power of each device.

First, when a data rate of input data of a beamforming block 310 is assumed to be the product (channel×A) of the number of channels and A (A is a positive number indicating the amount of data transmitted per unit time), a data rate of an output signal of each signal processing block is represented as A. In addition, a decimation ratio indicating a reduction rate of the amount of sampling data in a decimation block 340 is represented as r. Signal processing blocks processed in a probe and a signal processing stage are classified as follows.

(A) Output of beamforming block 310: A
(B) Output of quadrature demodulation block 330: 2A
(C) Output of decimation block 340: 2A/r
(D) Output of envelope detection block 350: A/r
(E) Output of digital scan converter block 380: bytes of width×height of output image For example, when communication conditions deteriorate, signal processing blocks from the beamforming block 310 to the decimation block 340 may be executed to make a data rate of 2A/r or signal processing blocks from the beamforming block 310 to the envelope detection block 350 may be executed to make a data rate of A/r in the probe stage such that a data rate necessary for transmission decreases. Alternatively, in case of worst communication conditions, signal processing blocks from the beamforming block 310 to the digital scan converter block 380 may be executed in the probe stage to decrease the data rate to bytes of width×height of an output image to provide an image at a uniform frame rate to the user. Furthermore, the user may determine weights in battery management such that any one of the receiving end and the transmitting end which has a sufficient battery power can process a larger amount of signals according to battery gauges of the receiving end and the transmitting end to affect determination of signal processing boundaries.

Figure 4:
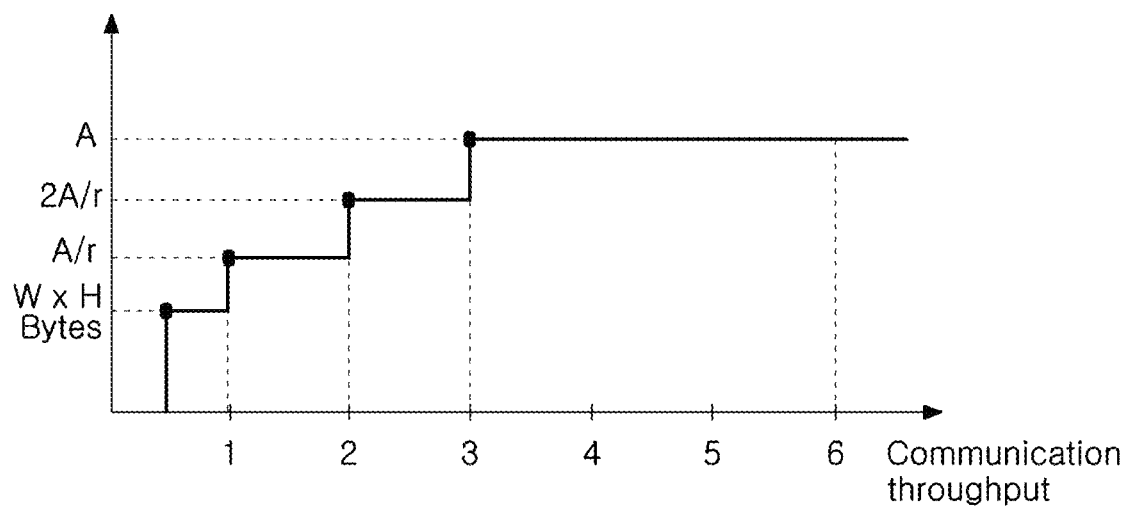
FIG. 4 is a diagram for describing a correlation between a data rate necessary to transmit medical image data and communication throughput in a communication network for which embodiments of the present invention are used.

FIG. 4 is a diagram for describing a correlation between a data rate necessary to transmit medical image data and communication throughput in a communication network for which embodiments of the present invention are used, wherein the horizontal axis represents communication throughput and the vertical axis represents a data rate necessary for data transmission.

The graph of FIG. 4 shows data rates necessary for data transmission when communication throughput is determined according to communication conditions and signal processing steps (signal path) to be processed in each processing stage (transmitting end or receiving end) are determined. As shown in FIG. 4, communication throughput and data rates necessary for data transmission have a positive correlation, and an appropriate data rate can be determined per communication throughput and used as a basis of determination of a signal path for each processing stage.

Figure 5:
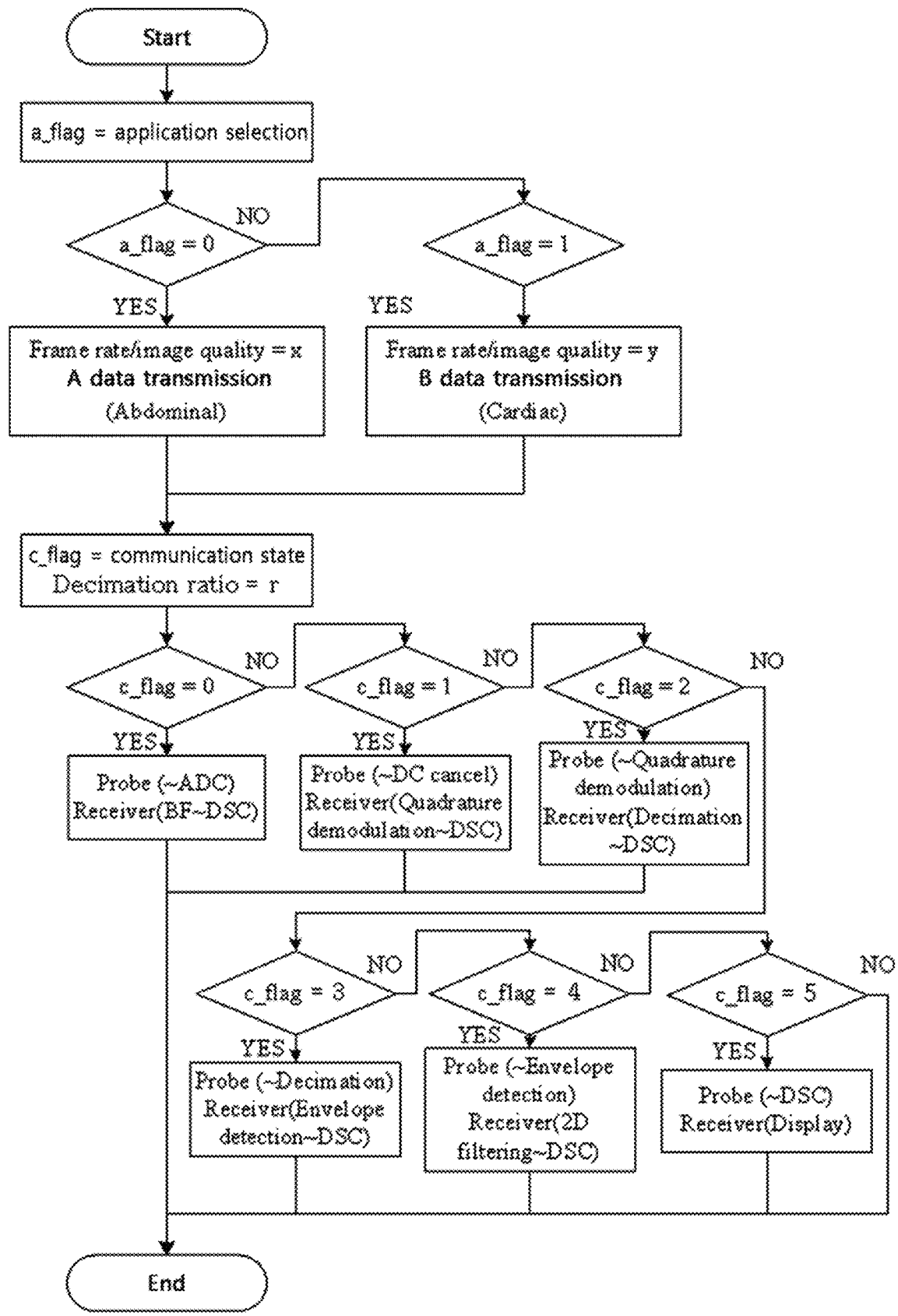
FIG. 5 is a diagram illustrating a variable data rate determination algorithm for transmitting medical image data depending on communication state, which is adopted in embodiments of the present invention.

FIG. 5 is a diagram illustrating a variable data rate determination algorithm for transmitting medical image data according to communication conditions, which is adopted by embodiments of the present invention.

First, when the wireless medical ultrasound system is started, the user selects an application (Abdomen or Cardiac) to be used. Information on a depth which will be basically observed is obtained through the application selected by the user, and thus a frame rate and image quality which can be provided under current communication conditions can be displayed through an example image according to weights of the frame rate and image quality selected by the user. Operations of the next step are performed on the basis of the weights of the frame rate and image quality determined by the user through the example image. Here, image quality is determined by the number of samples per millimeter in the axial direction.

Then, the algorithm detects a communication condition change time and adaptively changes signal processing steps performed in the transmitting end and the receiving end, and thus ultrasound image signal processing is performed. It is desirable to repeatedly perform this procedure whenever communication condition change is detected by the system. If communication conditions deteriorate and thus the frame rate and image quality set in the first step cannot be guaranteed, the data rate can be reduced by adjusting the decimation ratio r and the number of scanlines in consideration of the weights of the frame rate and image quality set by the user. Deterioration of image quality due to increase in the decimation ratio and decrease in the number of scanlines may be compensated for through interpolation at the receiving end.

Such adaptive signal path determination corresponds to a medical image processing procedure of step S240 described above with reference to FIG. 2. FIG. 5 illustrates a total of 6 signal paths, and those skilled in the art can modify such signal paths according to environments and conditions in which the medical imaging system is implemented. The aforementioned signal paths are exemplified as follows.

(1) A first signal path including an analog-to-digital converter (ADC) for the medical image data (2) A second signal path sequentially including the analog-to-digital converter, beamforming and DC cancellation (3) A third signal path sequentially including the analog-to-digital converter, beamforming, DC cancellation and quadrature demodulation (4) A fourth signal path sequentially including the analog-to-digital converter, beamforming, DC cancellation, quadrature demodulation and decimation (5) A fifth signal path sequentially including the analog-to-digital converter, beamforming, DC cancellation, quadrature demodulation, decimation and envelope detection (6) A sixth signal path sequentially including the analog-to-digital converter, beamforming, DC cancellation, quadrature demodulation, decimation, envelope detection and digital scan converter (DSC)

That is, one of the six signal paths is selected and medical image processing is performed through the selected signal path according to the algorithm illustrated in FIG. 5. Furthermore, when medical image data input from the probe is assumed to have a data rate A (A being a positive number indicating the amount of data transmitted per unit time) per channel (i.e., channel×A), an output signal of each signal path has the following characteristics.

(a) Data rate of output signal of first signal path: A
(b) Data rate of output signal of second signal path: A
(c) Data rate of output signal of third signal path: 2A
(d) Data rate of output signal of fourth signal path: 2A/r (r being a decimation ratio)
(e) Data rate of output signal of fifth signal path: A/r
(f) Data rate of output signal of sixth signal path: bytes of width×height of an output medical image Application examples in which the above-described embodiments of the present invention are applied to various situations will be proposed below.

Figure 6:
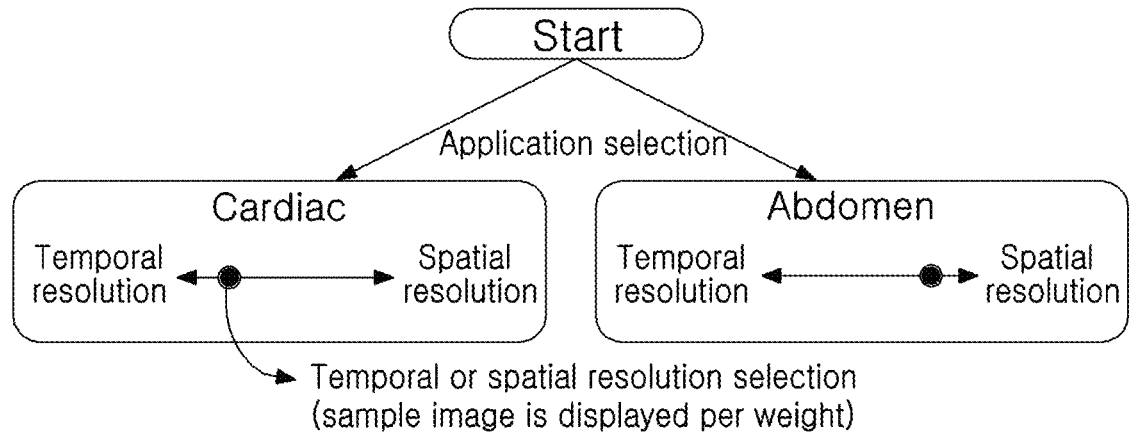
FIG. 6 is a diagram illustrating an example of implementing an application in the wireless ultrasound imaging system according to an embodiment of the present invention.

First, an application can be selected and frame rate/image quality weights can be set. FIG. 6 is a diagram illustrating an example of implementing an application in a wireless ultrasound imaging system according to an embodiment of the present invention. In FIG. 6, two applications (Cardiac and Abdomen) are assumed.

First, when the system is started, the user selects applications. When an application for observing the abdomen is selected, an observation depth is determined as 13 to 15 cm. The user can set desired weights for a frame rate and image quality. The system displays examples of images which can be provided under the current communication conditions according to the weights of the frame rate and image quality. The user determines frame rate and image quality weights while viewing the example images. To this end, weights can be selected using a control bar as shown in FIG. 6. In addition, a weight with respect to a degree of efficient battery distribution may also be determined.

Second, when communication conditions vary, images which satisfy a frame rate and image quality designated by the user are guaranteed and provided in spite of a change in communication conditions by varying signal processing boundaries of the transmitting end and the receiving end. In this case, it is assumed that communication conditions vary within a range in which the frame rate and image quality initially set by the user can be provided.

To this end, it is desirable that the image transmission device according to an embodiment of the present invention variably determine a data rate in proportion to detected communication throughput to induce a medical image processing result corresponding to a preset frame rate and image quality to be transmitted to the image reception device.

Third, when communication conditions seriously deteriorate, it is assumed that an image which satisfies the frame rate and image quality initially designated by the user cannot be provided even when the signal processing boundaries of the transmitting end and the receiving ends are varied. In this case, frame rate and image quality of a provided image are reduced by increasing the decimation ratio r and decreasing the number of scanlines. That is, when a communication throughput decrease below a threshold value due to variation in communication conditions is detected, the image transmission device controls the decimation ratio to be in inverse proportion to the detected communication throughput and controls the number of scanlines to be in proportion to the detected communication throughput so as to induce the medical image processing result to satisfy the preset frame rate and image quality.

Here, weights are assigned to the preset frame rate and image quality according to user selection. When a weight assigned to the frame rate is greater than a weight assigned to the image quality, the image transmission device can reduce the number of samples per millimeter while increasing the rate of increase in the decimation ratio and the rate of reduction in the number of scanlines.

On the contrary, when a weight assigned to the image quality is greater than a weight assigned to the frame rate, it is desirable that the image transmission device suppress a reduction in the number of samples per millimeter while maintaining the rate of increase in the decimation ratio and the rate of reduction in the number of scanlines, to thereby increase a frame rate reduction instead of minimizing image quality reduction. In this case, deterioration in image quality due to a decrease in the decimation ratio and an increase in the number of scanlines can be compensated for through interpolation at the receiving end.

Fourth, signal processing path selection of the transmitting end and the receiving end can be controlled in consideration of residual battery power. A large weight assigned to efficient distribution of battery power depending on battery gauges of the transmitting end and the receiving end has a great effect on one of the transmitting end and the receiving end which has a sufficient battery power and thus performs a larger number of signal processing steps in the process of changing the signal processing boundaries of the transmitting end and the receiving end according to communication conditions. On the contrary, a small weight assigned to efficient distribution of battery power depending on the battery gauges of the transmitting end and the receiving end has less effect on one of the transmitting end and the receiving end which has sufficient battery power and thus performs a larger number of signal processing steps in the process of changing the signal processing boundaries of the transmitting end and the receiving end according to communication conditions.

To this end, the image transmission device can receive residual battery information of the image reception device from the image reception device and compare the residual battery information thereof with the received residual battery information of the image reception device to control a signal path in consideration of the comparison result. Particularly, in the process of selecting a signal path and performing medical image processing, it is desirable to select the signal path such that any one of the image transmission device and the image reception device which has a relatively sufficient residual battery power performs a larger number of signal processing steps.

The above description focuses on the processes performed by the image transmission device. The following description will focus on processes performed by the image reception device corresponding to the image transmission device.

Figure 7:
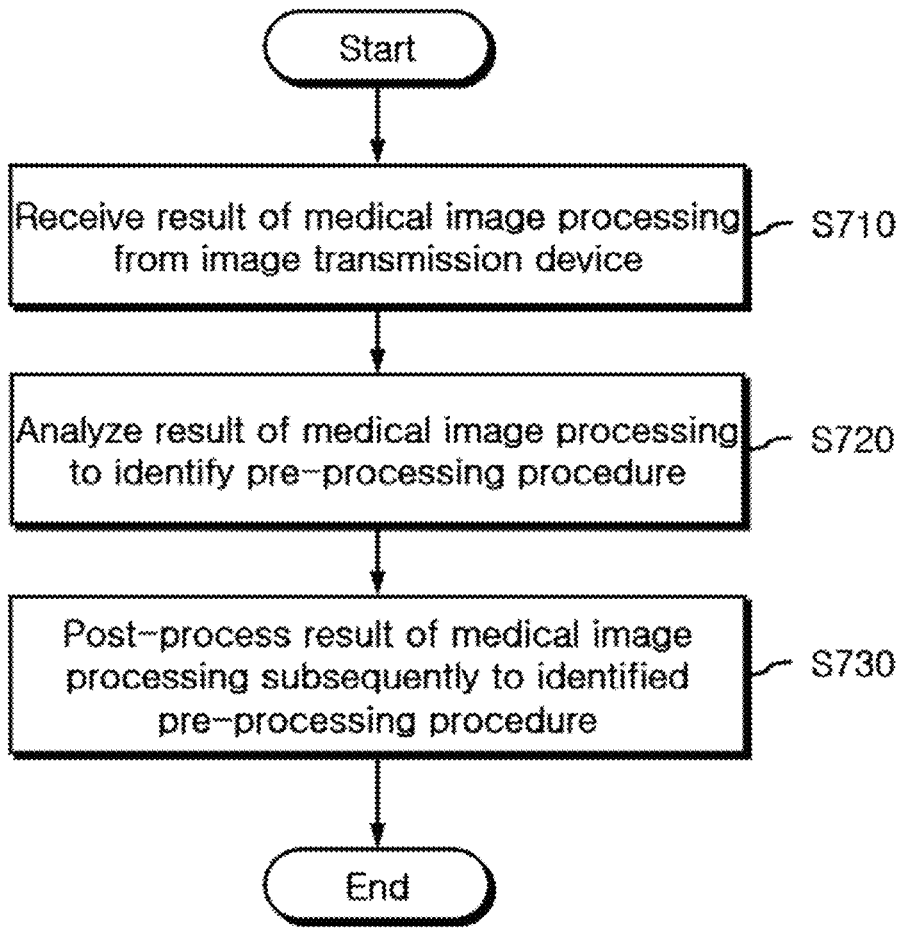
FIG. 7 is a flowchart illustrating a method of receiving a medical image by an image reception device in response to the image transmission device of FIG. 2 according to an embodiment of the present invention.

FIG. 7 is a flowchart illustrating a method of receiving a medical image by the image reception device according to an embodiment of the present invention in response to the image transmission device of FIG. 2. To avoid redundant description, corresponding components will be briefly described.

In step S710, the image reception device receives a medical image processing result from the image transmission device.

In step S720, the image reception device analyzes the medical image processing result received in step S710 to identify a pre-processing procedure. Here, the pre-processing procedure refers to a procedure performed by the image transmission device by receiving medical image data using a probe, detecting communication throughput indicating a communication state between the image transmission device and the image reception device, determining a data rate necessary for data transmission on the basis of a preset data rate based on the communication throughput and selecting a signal path satisfying the determined data rate for the medical image data. In addition, in the pre-processing procedure, the image transmission device may variably determine the data rate in proportion to the detected communication throughput to induce a result of medical image processing corresponding to a preset frame rate and image quality to be transmitted to the image reception device.

Identification of the pre-processing procedure can be simply performed by including an identifier or a special flag in the signal received through step S710. For example, the transmitting end (image transmission device) can transmit a flag indicating the final step of the pre-processing procedure or the receiving end (image reception device) can easily identify the pre-processing procedure through a method of receiving a unique identifier of a signal path selected in the pre-processing procedure.

In step S730, the image reception device post-processes the medical image processing result subsequently to the pre-processing procedure identified through step S720. This post-processing procedure refers to a signal processing procedure other than the pre-processing procedure in the entire wireless medical ultrasound image processing procedure. Accordingly, the post-processing procedure is determined in response to the previously performed pre-processing procedure.

Signal paths to which the pre-processing procedure and the post-processing procedure are assigned are exemplified as follows.

(1) When the pre-processing procedure corresponds to a first signal path including an analog-to-digital converter for medical image data, the image reception device sequentially performs post-processing of beamforming, DC cancellation, quadrature demodulation, decimation, envelope detection, digital scan conversion and image output.

(2) When the pre-processing procedure corresponds to a second signal path sequentially including an analog-to-digital converter, beamforming and DC cancellation, the image reception device sequentially performs post-processing of quadrature demodulation, decimation, envelope detection, digital scan conversion and image output.

(3) When the pre-processing procedure corresponds to a third signal path sequentially including an analog-to-digital converter, beamforming, DC cancellation and quadrature demodulation, the image reception device sequentially performs post-processing of decimation, envelope detection, digital scan conversion and image output.

(4) When the pre-processing procedure corresponds to a fourth signal path sequentially including an analog-to-digital converter, beamforming, DC cancellation and quadrature demodulation and decimation, the image reception device sequentially performs post-processing of envelope detection, digital scan conversion and image output.

(5) When the pre-processing procedure corresponds to a fifth signal path sequentially including an analog-to-digital converter, beamforming, DC cancellation and quadrature demodulation, decimation and envelope detection, the image reception device sequentially performs post-processing of digital scan conversion and image output.

(6) When the pre-processing procedure corresponds to a sixth signal path sequentially including an analog-to-digital converter, beamforming, DC cancellation and quadrature demodulation, decimation, envelope detection and digital scan conversion, the image reception device performs post-processing of image output.

When medical image data input from the probe is assumed to have a data rate A (A being a positive number indicating the amount of data transmitted per unit time) per channel (i.e., channel×A), an output signal of each signal path has the following characteristics.

(a) Data rate of output signal of pre-processing procedure according to first signal path: A (b) Data rate of output signal of pre-processing procedure according to second signal path: A (c) Data rate of output signal of pre-processing procedure according to third signal path: 2A (d) Data rate of output signal of pre-processing procedure according to fourth signal path: 2A/r (r being a decimation ratio)

(e) Data rate of output signal of pre-processing procedure according to fifth signal path: A/r (f) Data rate of output signal of pre-processing procedure according to sixth signal path: bytes of width×height of output medical image Furthermore, the aforementioned image reception device can transmit residual battery information thereof to the image transmission device to induce the image transmission device to compare residual battery information of the image transmission device with the received residual battery information of the image reception device and to control a signal path in consideration of the comparison result to determine the pre-processing procedure. Particularly, in the pre-processing procedure, it is desirable to select the signal path such that any one of the image transmission device and the image reception device which has relatively sufficient residual battery power performs a larger number of signal processing steps.

(2) Second Embodiments

The second embodiments of the present invention propose a medical imaging system in which a probe that generates ultrasound waves and can receive ultrasound waves generated from the human body is separately configured, and a remote medical imaging device connected to the probe performs ultrasound image processing and then transmits the ultrasound image processing result to a local medical imaging device through wired/wireless communication such that a doctor can acquire a final ultrasound image with respect to conditions of a remotely located patient. Problems expected in implementation of this remote medical imaging system are as follows.

When an ultrasound imaging system using a wireless ultrasound probe is implemented, throughput is limited due to the limitations of the current communication technology and user experience is remarkably deteriorated and thus utility can be restricted. Particularly, states of communication media connected to a transmitting end which includes a probe or is connected thereto and a receiving end may be varied, and in the case of wireless communication, various faults may occur according to working environments. Accordingly, there is a need for ultrasound equipment which guarantees image quality high enough to be diagnosed by a user while reducing the amount of data transmitted from wireless ultrasound equipment capable of efficiently detecting signals.

Embodiments of the present invention which will be described below propose technical means for providing image segmentation in terms of user experience using various techniques capable of reducing the amount of data, such as a data rate, temporal resolution and data compression, and efficiently providing diagnostic images through a user-friendly control method as a technology of providing maximum user experience in limited communication conditions of a wireless ultrasound diagnostic system.

There are various methods of reducing the amount of data. The amount of data may be reduced through decimation which decreases the amount of sampling data or the amount of temporally input data may be reduced by decreasing a frame rate of an image. In addition, a communication bandwidth may be reduced through data compression. However, a method of simultaneously applying such data reduction methods to all original images may deteriorate user experience. Particularly, medical images include important information that needs to be maintained with high image quality in a specific region thereof in many cases, and thus across-the-board image quality deterioration may cause serious problems for a user and a patient.

Accordingly, the embodiments of the present invention which will be described below can minimize the amount of data to be wirelessly transmitted by segmenting an acquired medical image, providing a region of interest (ROI) of a user with high image quality and decreasing image quality of other regions. That is, the embodiments of the present invention propose a technique of acquiring clinical information from a patient through a remote ultrasound (US) system having an ultrasound probe attached thereto and transmitting the acquired data to a separate local US system in proximity to the view of a user in a wireless communication network having a limited bandwidth, wherein information obtained by the user is maintained while the amount of data is minimized. Particularly, the embodiments of the present invention reduce the amount of actually transmitted data by adopting a method of dividing an image provided to the user into various stages on the basis of a main observation region of interest and gradually decreasing data quality through the stages, thereby securing a communication bandwidth and maximizing user experience.

Hereinafter, the second embodiments of the present invention will be described in detail with reference to the drawings.

As described above, FIG. 1 illustrates the configuration commonly adopted by the embodiments of the present invention, and thus review of the configuration illustrated in FIG. 1 will focus on components for transmitting and receiving medical images in terms of image segmentation.

FIG. 1 is a block diagram illustrating a schematic structure of a wireless ultrasound imaging system according to another embodiment of the present invention, which includes a medical image transmission system/remote ultrasound (US) system 10 and a medical image reception system/local ultrasound (US) system 20.

In this system structure, acquisition of an ultrasound signal is performed through the probe 11 connected to the remote US system 10, and acquired image data is subjected to a series of image processing procedures in the remote US system 10 and then transmitted to the local US system 20. Here, if a communication rate is limited due to the distance between the systems 10 and 20 or other interference, it is difficult to transmit generated original image data in its entirety and, simultaneously, secure maximum performance, as described above.

In the remote US system 10, the processor 13 receives medical image data using the probe 11. The communication unit 15 of the image transmission device 10 transmits a medical image to the local US system 20 or detects communication throughput indicating a communication state between the image transmission device 10 and the image reception device 20 and provides the communication throughput to the processor 13. The processor 13 generates a medical image through a series of ultrasound image signal processing procedures, sets a region of interest (ROI) in the generated medical image, and segments the medical image into one or more regions according to distances from the set ROI. In addition, the processor 13 generates reduced image data for each segmented region by applying a differential image data reduction technique to the segmented regions. Then, the remote US system 10 transmits the reduced medical image to the local US system 20 through the communication unit 15. Further, the processor 13 may apply the differential image data reduction technique to the segmented regions on the basis of communication throughput detected through the communication unit 11. That is, if currently available communication throughput is low, it is desirable to use a reduction technique having a higher data reduction rate.

The local US system 20 receives the medical image from the remote US system 10 through the communication unit 25. Then, the processor 23 of the local US system 20 analyzes the received medical image to reconstruct reduced image data per segmented region. Here, the local US system 20 directly outputs the image data to the display device 30 when the image data can be reconstructed without a special decoding process. However, if the image data has been encoded by means of a specific compression algorithm, a process of decoding the image data using a decoding algorithm corresponding to the compression algorithm is required. Accordingly, the processor 23 of the local US system 20 needs to identify the image data reduction technique with respect to the reduced image data in analysis of the received medical image.

Furthermore, controllers 17 and 27 may be connected to both the remote US system 10 and the local US system 20 or connected to any one thereof. These controllers 17 and 27 may be implemented as gyro sensors which automatically track movement of the probe 11 or buttons, jog wheels or the like which can be directly controlled by a user in consideration of image quality and temporal resolution. The controllers 17 and 27 deliver a command for requesting image data quality change to the remote US system 10 or the local US system 20 to induce the system to apply an image data reduction technique which satisfies the received command. For example, the command for requesting image data quality change is set in consideration of a degree of image changes between frames in the medical image or a degree of movement of the probe 11 and may be a command for controlling temporal resolution of the medical image.

Figure 8:
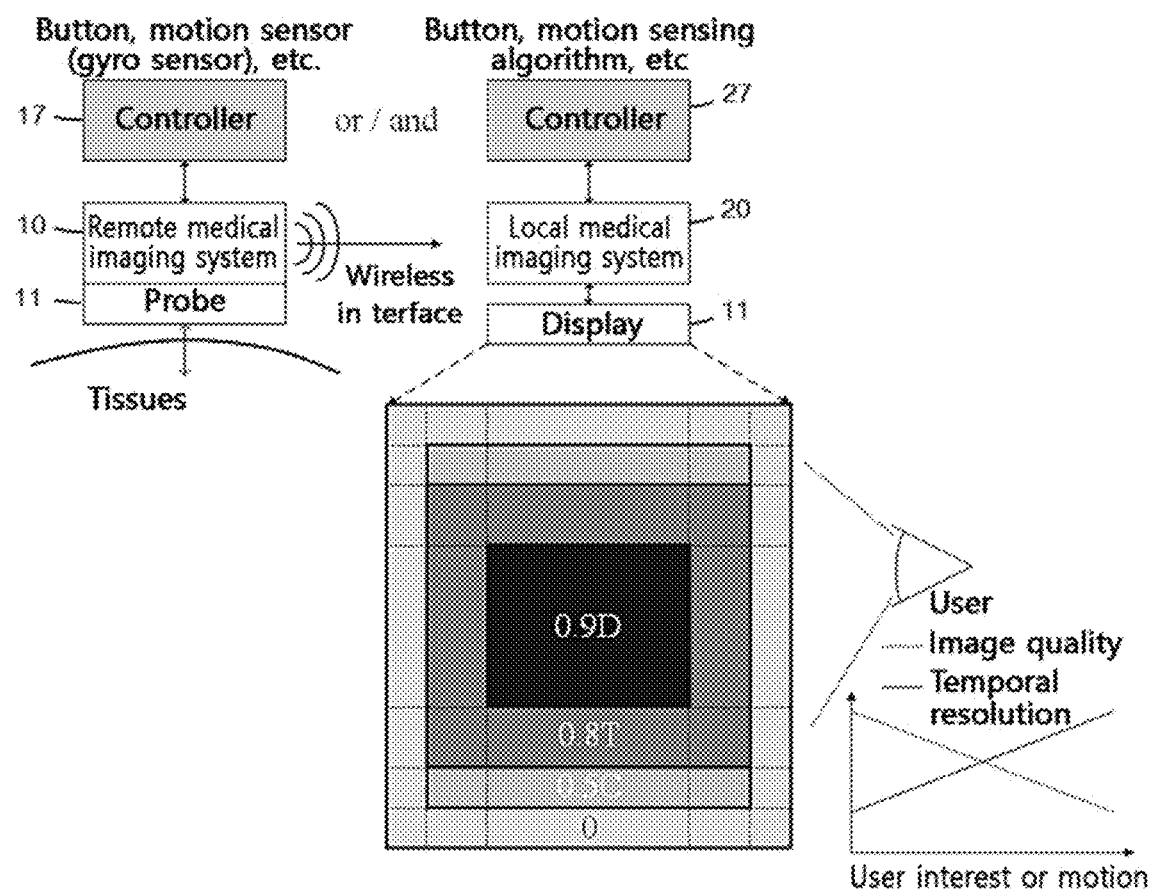
FIG. 8 is a diagram for describing a method of transmitting image data reduced through region segmentation using a region of interest in a wireless ultrasound imaging system according to another embodiment of the present invention.

FIG. 8 is a diagram for describing a method of transmitting image data reduced through region segmentation using an ROI in a wireless ultrasound imaging system according to another embodiment of the present invention.

When it is assumed that the center of an image displayed through the display 11 of the local US system 20 is set as an ROI, the quality of a final medical image can be determined by segmenting the image into regions in a direction with increasing distance from the center of the image on the basis of the center of the image and adjusting the quantity and quality of data per segmented region. Here, D represents image data reduction through data decimation, T represents image data reduction through time decimation and C represents image data reduction through data compression.

In addition, a numeral in the range of 0 to 1 marked before each sign is a data weight indicating a data reduction rate in data performance provided by the remote US system 10. For example, a weight of "1" represents that transmitted data is used, and a weight of "0" represents that image data with respect to the region corresponding to the weight is not transmitted and thus an image is not displayed.

Further, a tradeoff between the quantity and quality of data can be controlled using the controllers 17 and 27 connected to both or one of the remote US system 10 and the local US system 20. The controllers 17 and 27 may be implemented as physical buttons or jog wheels or implemented as measurement devices such as a gyro sensor.

Referring to FIG. 8, it can be known that image quality and temporal resolution are inversely proportional to each other. The image quality and temporal resolution may be controlled according to requirements of a user, set values according to diagnosis, or a differential image data reduction technique applied to the ROI and segmented regions. For example, when an image output from the local US system 20 has many abrupt motions or a doctor needs to rapidly move the probe 11 of the remote US system 10 in order to detect the affected area, alarm information indicating that image data needs to be reduced to increase temporal resolution may be provided. On the contrary, when the probe 11 is less moved or a doctor wants to closely monitor the affected area, alarm information indicating that an image with high quality needs to be provided even at the expense of temporal resolution may be provided. Through such divided operations, information on the amount of data that needs to be processed for one or more steps may be preset.

In summary, the embodiments of the present invention can segment an image into regions and variably control the amount of data to be transmitted per segmented region to optimize the amount of entire data. In addition, a method of reducing data or a degree to which data is reduced may be selected as necessary. An image data reduction technique to be applied and a weight are assigned per segmented region and a degree of data reduction is determined according to the image data reduction technique. Division (segmentation) of an image into regions may be designated by a preset value of the system or implemented with a user set value, and the entire image may be set as one region as necessary.

For example, when communication conditions are satisfactory, the number of segmentations is reduced and a maximum weight (e.g., "1") is assigned to the entire image to achieve best performance. On the contrary, when communication conditions deteriorate, a minimum weight (e.g., "0") may be assigned to regions other than an ROI such that data with respect to the regions is not transmitted to the local US system in order to extremely reduce the amount of data. In this case, the user can receive and view only the ROI as if they were using leading glasses.

Image quality decreased according to a data reduction method can be enhanced using an image correction algorithm in the local US system 20. For example, when data reduction is achieved through data decimation, the local US system 20 can enhance image quality through post-processing such as spatial image interpolation. When temporal resolution is sacrificed, a frame rate of images can be recovered using temporal interpolation.

Figure 9:
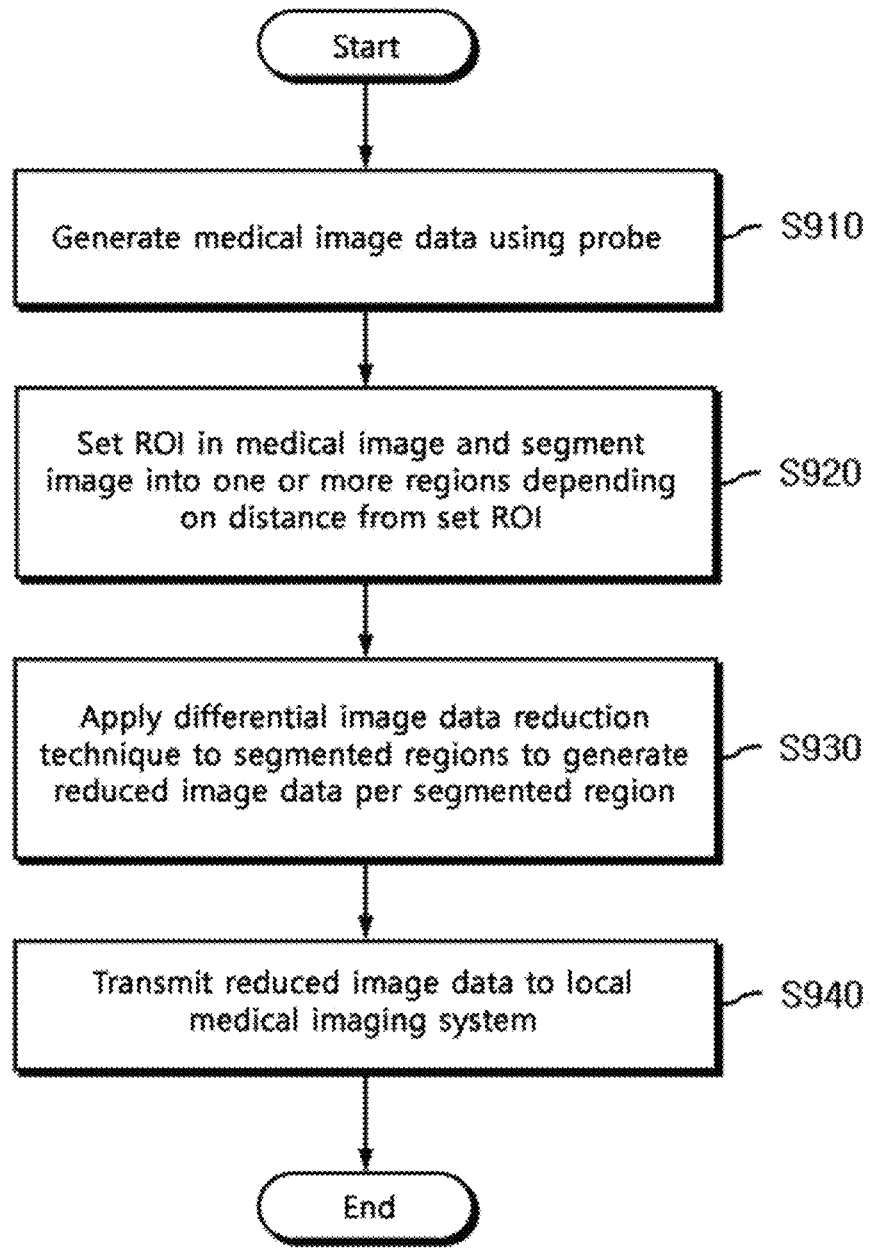
FIG. 9 is a flowchart illustrating a method of adaptively transmitting a medical image by a remote medical imaging system using image segmentation according to another embodiment of the present invention.

FIG. 9 is a flowchart illustrating a method of transmitting a medical image on the basis of the remote US system according to another embodiment of the present invention. The method includes the following steps.

In step S910, the remote US system generates a medical image using a probe.

In step S920, a region of interest (ROI) is set in the medical image generated in step S910 and the medical image is segmented into one or more regions in a direction with increasing distance from the ROI.

In step S930, the remote US system applies a differential image data reduction technique to the regions segmented in step S920 to generate reduced image data per segmented region. Here, it is desirable to differentially apply an image data reduction technique which has a higher data reduction rate for a segmented region separated from the ROI than the ROI in the process of generating reduced image data.

The differential image data reduction technique may be any one of data decimation, temporal decimation and data compression for each segmented region. In addition, the differential image data reduction technique preferably assigns a lower image weight to a segmented region separated from the ROI than the ROI.

In step S940, the remote US system transmits the image data reduced in step S930 to the local US system.

In another aspect of the present invention, the method of transmitting a medical image illustrated in FIG. 9 may further include a process of measuring a communication state between the remote US system and the local US system prior to step S930. Accordingly, in step S930 of generating reduced image data, an image data reduction technique can be applied in consideration of communication throughput according to the measured communication state. Such a differential image data reduction technique preferably assigns an image weight in proportion to communication throughput.

Furthermore, in another aspect of the present invention, the method of transmitting a medical image illustrated in FIG. 9 may further include a process of receiving, by the remote US system, a command for requesting image data quality change prior to step S930. Accordingly, in step S930 of generating reduced image data, an image data reduction technique which satisfies the received command may be applied. In addition, the command for requesting image data quality change is set in consideration of a degree of image changes between frames in the medical image or a degree of movement of the probe and may be implemented as a command for controlling temporal resolution of the medical image.

Hereinafter, application examples based on various image data reduction techniques using the above-described other embodiments of the present invention will be proposed.

Figure 10A:
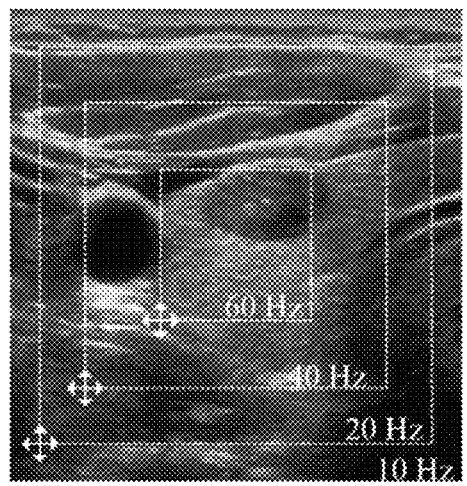
FIGS. 10a to 10c are diagrams illustrating application examples of a differential image data reduction technique in the wireless ultrasound imaging system according to another embodiment of the present invention.
Figure 10B:
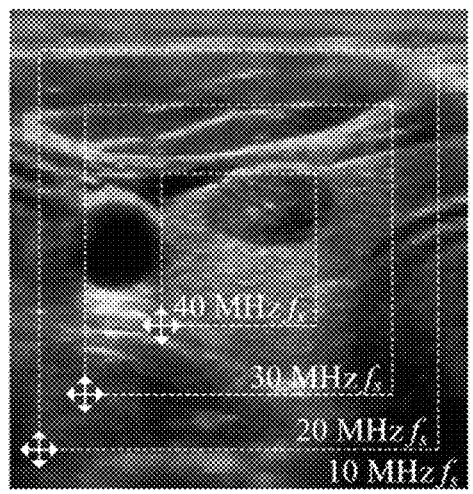
Figure 10C:
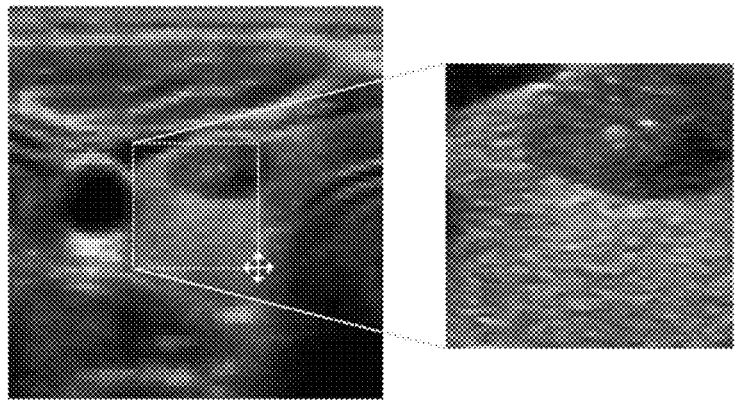

FIGS. 10a to 10c are diagrams illustrating examples of applying a differential image data reduction technique in the wireless ultrasound imaging system according to the other embodiments of the present invention. FIG. 10a shows a result obtained when a temporal resolution varying technique is applied, FIG. 10b shows a result obtained when a data rate varying technique is applied, and FIG. 10c shows a result obtained when a technique of setting a weight of "0" for all regions other than a specific region (e.g., a central region or an ROI) is applied.

Referring to FIG. 10a, it can be confirmed that segmentation is performed in a direction from the central ROI to the edge, highest temporal resolution (60 Hz) is assigned to the center, and lowest temporal resolution (10 Hz) is assigned to the outmost region through gradual reduction. Referring to FIG. 10b, it can be confirmed that segmentation is performed in a direction from the central ROI to the edge, a highest data rate (40 MHzfs) is assigned to the center, and a lowest data rate (10 MHzfs) is assigned to the outmost region through gradual reduction. In addition, it can be confirmed that image quality of the outmost region is deteriorated. Referring to FIG. 10c, it can be confirmed that the image is segmented into the central ROI and the remaining region and a weight of "0" is assigned to the remaining region other than the central ROI. As a result, the local US system cannot receive an image corresponding to the region other than the ROI.

As described above, various segmentation methods, image data reduction techniques and weight application methods can be used for a medical image. If an image is segmented into two regions having the same area as a simple example, when temporal resolution for a region other than an ROI is set to half (25 Hz) of temporal resolution (50 Hz) for the ROI, the amount of transmitted data can be reduced by 25% compared to a case in which the entire data is transmitted. The same effect is obtained when a data rate for the region other than the ROI is reduced under the same conditions.

Figure 11:
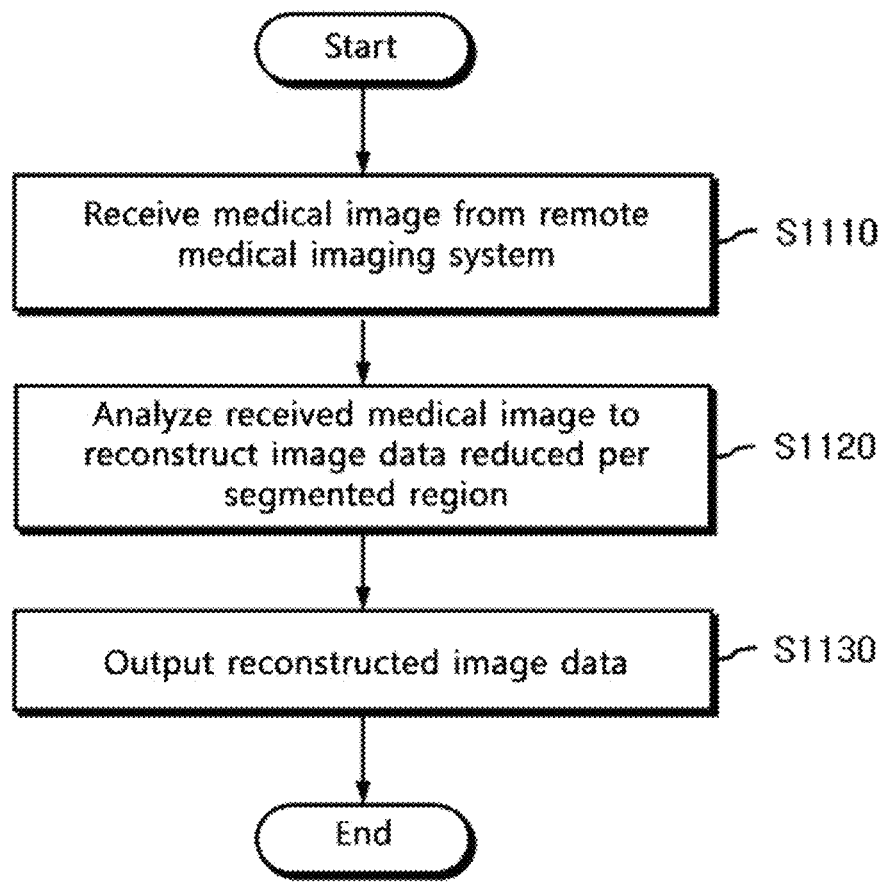
FIG. 11 is a flowchart illustrating a method of receiving a medical image by a local medical imaging system according to another embodiment of the present invention.

FIG. 11 is a flowchart illustrating a method of receiving a medical image by the local US system according to another embodiment of the present invention in response to the remote US system of FIG. 9. To avoid redundant description, corresponding components will be briefly described.

In step S1110, the local US system receives a medical image from the remote US system.

In step S1120, the local UE system analyzes the medical image received in step S1110 to reconstruct image data reduced per segmented region. Here, the reduced image data has been generated by the remote US system by generating the medical image using a probe, setting an ROI in the generated medical image, segmenting the medical image into one or more regions depending on distance from the set ROI and applying a differential image data reduction technique to the segmented regions. The reduced image data is generated by differentially applying an image data reduction technique having a higher data reduction rate for a segmented region separated from the ROI than the ROI.

In addition, the differential image data reduction technique can employ any one of data decimation, temporal decimation and data compression for each segmented region, and it is desirable to assign a smaller image weight to a segmented region separated from the ROI than the ROI.

If the differential image data reduction technique corresponds to data decimation, the local US system can perform spatial image interpolation on the reconstructed image data to improve image quality. If the differential image data reduction technique corresponds to temporal decimation, the local US system can perform temporal interpolation on the reconstructed image data to recover a frame rate of the image.

The reduced image data may be generated by measuring a communication state between the remote US system and the local US system and applying an image data reduction technique in consideration of communication throughput according to the measured communication state, and the differential image data reduction technique preferably assigns an image weight in proportion to the communication throughput.

Furthermore, the reduced image data may be generated by the remote US system by receiving a command for requesting image data quality change and applying an image data reduction technique which satisfies the received command. The command for requesting image data quality change is set in consideration of a degree of image changes between frames in the medical image or a degree of movement of the probe and is preferably a command for controlling temporal resolution of the medical image.

Instep S1130, the local US system outputs the image data reconstructed in step S1120.

(3) Third Embodiments

Third embodiments of the present invention propose technical means for reducing the size of data used for operations and communication when communication conditions deteriorate or residual power is exhausted in a portable medical ultrasound imaging technique. To this end, data reduction techniques adopted by embodiments of the present invention improve compression efficiency in a data reconstruction process by controlling a parameter for reconstructing an ultrasound image, use various methods such as a data rate, temporal resolution and data compression for image segmentation, or provide a technical means for reducing a data rate to improve a frame rate and extending system available time through efficient distribution of use of batteries.

The third embodiments of the present invention will be described in detail with reference to the drawings.

As described above, FIG. 1 illustrates the configuration commonly adopted by the embodiments of the present invention, and thus review of the configuration illustrated in FIG. 1 will focus on components for transmitting and receiving medical images in terms of control of a reconstruction parameter and compression.

In FIG. 1, the processor 13 of the image transmission device 10 acquires medical image data using the probe 11. The communication unit 15 of the image transmission device 10 detects at least one of a communication state and a power state between the image transmission device and the image reception device and provides the detection result to the processor 13. Then, the processor 13 evaluates the communication state or power state provided thereto, determines a reconstruction parameter for reconstructing an image according to the evaluation result and reconstruct a first medical image from the acquired medical image data according to the determined reconstruction parameter. Here, the reconstruction parameter is preferably at least one of a dynamic range, contrast, gain, amplitude threshold, sharpness and resolution with respect to the medical image. Then, the processor 13 of the image transmission device 10 encodes the reconstructed first medical image to generate compressed data. A series of operations performed in the image transmission device 10 corresponds to an image pre-processing procedure performed in the transmitting end of the medical imaging system. Subsequently, the image transmission device 10 transmits the generated compressed data to the image reception device 20 through the communication unit 15 to induce the image reception device 20 to generate a post-processed second medical image from the compressed data.

In FIG. 1, the image reception device 20 receives the compressed data from the image transmission device 10 through the communication unit 25. Then, the processor 23 of the image reception device 20 decodes the received compressed data to reconstruct a first medical image. Subsequently, the processor 23 of the image reception device 20 analyzes the reconstructed first medical image to identify a pre-processing procedure and then performs a post-processing operation according to the identification result to generate a second medical image. Here, the pre-processing procedure refers to the procedure of generating the first medical image performed by the image transmission device 10. The processor 23 performs a post-processing procedure on the medical image processing result received through the communication unit 25 subsequently to the identified pre-processing procedure. This post-processing procedure refers to the remaining part of the entire procedure for generating a final medical image signal from the original signal acquired through the probe 11 except the pre-processing procedure performed by the image transmission device 10. Finally, the processor 23 outputs the post-processed final medical image (second medical image) to the display device 30.

Figure 12:
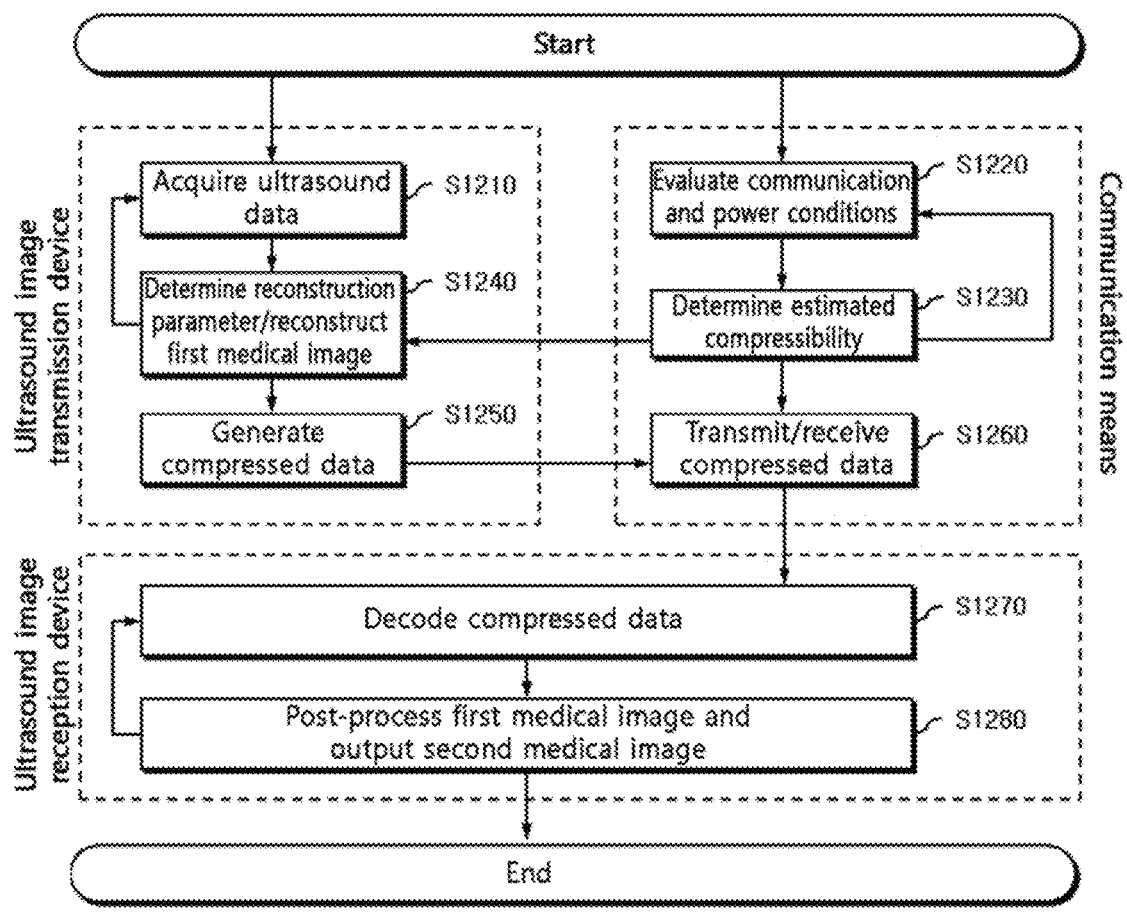
FIG. 12 is a flowchart illustrating a process of adaptively reconstructing and transmitting/receiving a medical image on the basis of communication and power conditions in a wireless ultrasound imaging system according to another embodiment of the present invention.

FIG. 12 is a flowchart illustrating a process of reconstructing, transmitting and receiving a medical image in the wireless ultrasound imaging system according to another embodiment of the present invention.

In an ultrasound image transmission device, ultrasound data is acquired using a probe in step S1210. In parallel with acquisition of the ultrasound data, a communication means included in the ultrasound image transmission device and an ultrasound image reception device evaluate current wireless communication and power conditions in step S1220. For example, preset multilevel evaluation per section can be performed. Estimated compressibility is determined on the basis of the evaluation result in step S1230. The estimated compressibility refers to a degree to which an ultrasound data measurement value acquired by the ultrasound image transmission device will be compressed. In reconstruction of the ultrasound data acquired above in S1240, a specific reconstruction parameter, for example, a dynamic range, a contrast, a gain, an amplitude threshold, image sharpness, resolution and the like, determined in step S1230 according to communication conditions or power conditions for each section measured in step S1220 are used. Here, it is desirable that the specific reconstruction parameter be determined in advance such that the reconstruction parameter has image characteristics capable of satisfying the estimated compressibility according to a compression method to be performed.

Reconstructed data (first medical image) generated in step S1240 is reduced in quantity through a designated compression method in step S1250 and delivered to the ultrasound image reception device through step S1260.

The ultrasound image reception device decodes the compressed data delivered thereto into the original reconstructed data (first medical image) in step S1270, performs post-processing on the reconstructed data to generate a final ultrasound image (second medical image) and then outputs the final ultrasound image to the user in step S1280.

The data compression efficiency in the above-described embodiments may be optimized by segmenting an image into regions in terms of user experience and image quality and compressing the regions to different degrees or by selectively changing data to be compressed and transmitted. Each embodiment will be described in more detail with reference to the drawings.

Figure 13:
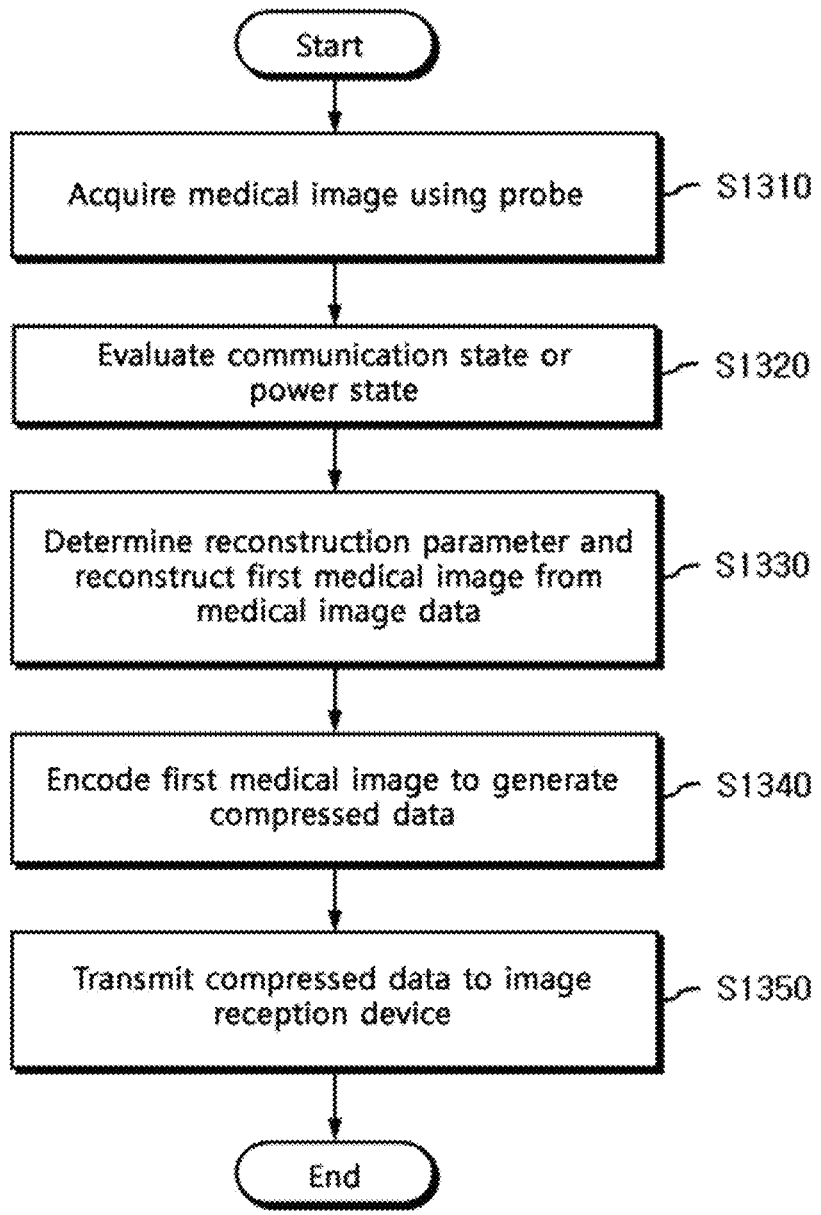
FIG. 13 is a flowchart illustrating a method of transmitting a medical image by an image transmission device according to another embodiment of the present invention.

FIG. 13 is a flowchart illustrating a method of transmitting a medical image by an image transmission device according to another embodiment of the present invention.

In step S1310, the image transmission device acquires medical image data using a probe.

In step S1320, the image transmission device evaluates at least one of a communication state and a power state between the image transmission device and an image reception device. Throughput according to a communication state may be detected using various communication channel detection techniques used in network technology fields, and communication state indexes proposed in wired or wireless communication standards may be used.

In step S1330, the image transmission device determines a reconstruction parameter according to the result of evaluation of step S1320 and reconstructs a first medical image from the medical image data according to the reconstruction parameters. As described above, it is desirable that the reconstruction parameter be at least one of a dynamic range, contrast, gain, amplitude threshold, sharpness and resolution with respect to the medical image. In addition, it is desirable to variably determine the reconstruction parameter for image reconstruction such that the size of the first medical image is proportional to throughput according to the communication state or residual power according to the power state in the process of reconstructing the first medical image.

In step S1340, the image transmission device encodes the first medical image reconstructed in step S1330 to generate compressed data. In generation of the compressed data, various embodiments of the present invention can use a technique of segmenting an image into regions in terms of user experience and image quality and optimization techniques of selectively changing data to be compressed and transmitted in the ultrasound signal processing step.

In step S1350, the image transmission device transmits the compressed data generated in step S1340 to the image reception device to induce the image reception device to generate a post-processed second medical image from the compressed data.

Figure 14:
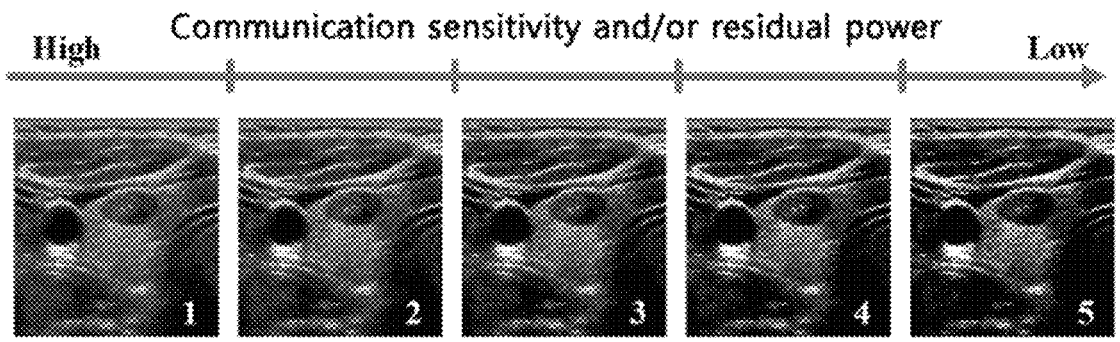
FIG. 14 is a diagram illustrating a process of reconstructing an image according to communication and power conditions.

FIG. 14 is a diagram illustrating an image reconstruction process according to communication and power conditions and shows reconstructed data generated by pre-configuring reconstruction parameters for each communication condition and power condition and then selecting a reconstruction parameter suitable for the current condition. Although it is desirable to maintain the quality of reconstructed data at a highest level as long as communication conditions or power conditions allow, different strategies may be adopted according to given environments.

In FIG. 14, only a dynamic range of the image among various available reconstruction parameters was corrected to vary the amount of clinical information represented in the image and the varied amount of clinical information was applied. Referring to FIG. 14, it can be confirmed that information represented in images is reduced with the progress from the first stage to the fifth stage, that is, in a direction in which communication sensitivity or residual power decreases but all images provide minimum information necessary for diagnosis.

Figure 15:
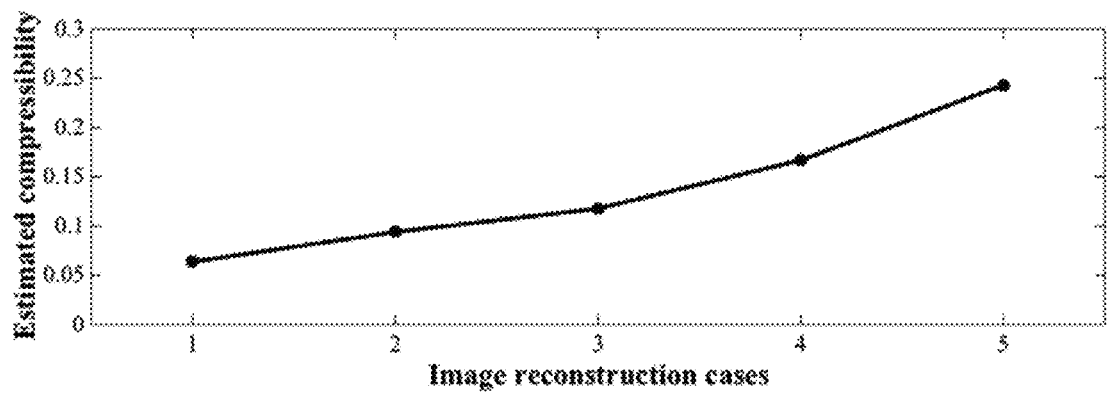
FIG. 15 is a diagram illustrating estimated compressibility with respect to each image reconstruction process.

FIG. 15 is a diagram illustrating estimated compressibility for each image reconstruction case and shows estimated compressibility when data reconstructed through multiple stages is compressed through run-length encoding (RLE) compression which is a typical compression method. The x-axis represents that the amount of reconstructed data decreases with progress from case 1 to case 5 and the y-axis represents that estimated compressibility when the reconstructed data is compressed varies from 6% to 25%. It can be confirmed from FIG. 15 that user experience can be achieved while the amount of data to be transmitted is reduced.

Hereinbelow, two techniques with respect to image segmentation and selective application of ultrasound signal processing steps in terms of compression efficiency will be described.

3-1) Image Segmentation Technique

In the medical image transmission method of FIG. 13 according to another embodiment of the present invention, the first medical image may be segmented into at least two regions and a differential image reduction technique may be applied per segmented region to generate compressed image data in step S1340 of generating compressed data. Here, the process of generating reduced image data may be achieved by applying different image data reduction techniques to the segmented regions such that segmented regions other than a region set as an ROI have higher data compressibility in proportion to distance from the ROI. Particularly, such a differential image data reduction technique can employ one of data decimation, temporal decimation and data compression for each segmented region. Image quality deteriorated according to data reduction method can be enhanced using an image correction algorithm in an ultrasound reception device. For example, the ultrasound reception device can enhance image quality through post-processing such as spatial image interpolation when data reduction is performed through data decimation and recover a frame rate of images using temporal interpolation when temporal resolution is sacrificed.

3-2) Technique of Selective Application of Ultrasound Signal Processing

In the medical image transmission method of FIG. 13 according to another embodiment of the present invention, a data rate necessary for data transmission may be determined according to an evaluation result and a signal path satisfying the determined data rate may be selected to generate compressed image data in step S1340 of generating compressed data. Here, in the compressed data generation process, the data rate is variably determined in proportion to throughput according to a communication state or residual power according to a power state to induce compressed data corresponding to a preset frame rate and image quality to be transmitted to an image reception device.

If communication throughput decreases below a first threshold value due to communication state variation or residual power decreases below a second threshold value due to power state variation, it is desirable to control a decimation ratio to be inversely proportional to the communication throughput or the residual power and to control the number of scanlines to be proportional to the communication throughput or the residual power in the compressed data generation process.

Meanwhile, the frame rate and image quality may be respectively assigned weights according to user selection. When a larger weight is assigned to the frame rate than the image quality, it is desirable that the image transmission device decrease the number of samples per length while increasing the rate of increase in the decimation ratio and the rate of reduction in the number of scanlines. When a larger weight is assigned to the image quality than the frame rate, it is desirable that the image transmission device suppress a reduction in the number of samples per length while maintaining the rate of increase in the decimation ratio and the rate of reduction in the number of scanlines.

Figure 16:
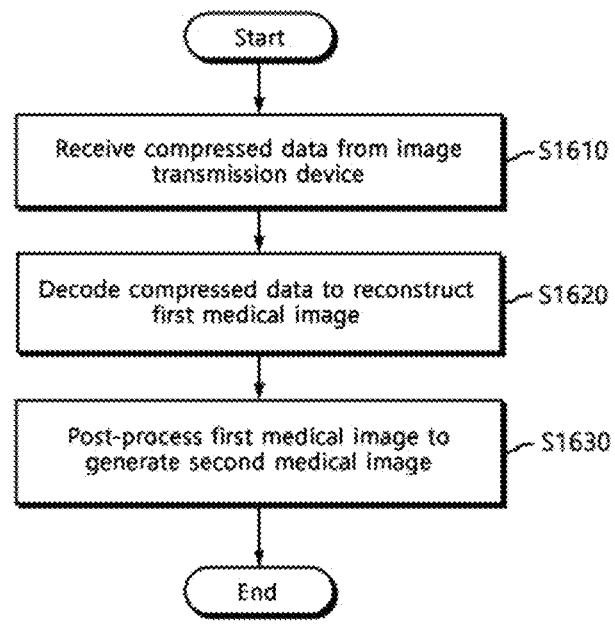
FIG. 16 is a flowchart illustrating a method of receiving a medical image by an image reception device according to another embodiment of the present invention.

FIG. 16 is a flowchart illustrating a method of receiving a medical image by an image reception device according to another embodiment of the present invention. FIG. 16 time-sequentially shows a method of processing a medical image in response to the operation of the image transmission device of FIG. 13. To avoid redundant description, corresponding components will be briefly described.

In step S1610, the image reception device receives compressed data from the image transmission device. Here, the compressed data is generated by the image transmission device by acquiring medical image data using a probe, evaluating at least one of a communication state and a power state between the image transmission device and the image reception device, determining a reconstruction parameter depending on the evaluation result, reconstructing a first medical image from the medical image data according to the determined reconstruction parameter and encoding the reconstructed first medical image. The reconstruction parameter is variably determined such that the size of the first medical image is proportional to throughput according to the communication state or residual power according to the power state.

First, in the case of implementation using the image segmentation technique, the compressed data can be generated by the image transmission device by segmenting the first medical image into at least two regions and applying a differential image data reduction technique per segmented region such that segmented regions other than a region set as an ROI have higher data compressibility in proportion to distance from the ROI. Here, the differential image data reduction technique may employ one of data decimation, temporal decimation and data compression for each segmented region. It is desirable that the medical image reception device perform spatial image interpolation on the first medical image when data decimation is employed as the differential image data reduction technique and perform temporal interpolation on the reconstructed first medical image when temporal decimation is employed as the differential image data reduction technique.

Second, in the case of implementation using the technique of selective application of ultrasound signal processing, the compressed data can be generated by the image transmission device according to a preset frame rate and image quality by determining a data rate necessary for data transmission depending on the evaluation result and selecting a signal path which satisfies the determined data rate, wherein the data rate is variably determined in proportion to throughput according to the communication state or residual power according to the power state. If communication throughput decreases below a first threshold value due to communication state variation or residual power decreases below a second threshold value due to power state variation, the compressed data can be generated by controlling a decimation ratio to be inversely proportional to the communication throughput or the residual power and controlling the number of scanlines to be proportional to the communication throughput or the residual power. Meanwhile, the frame rate and image quality are respectively assigned weights according to user selection. When a larger weight is assigned to the frame rate than the image quality, the image transmission device may decrease the number of samples per length while increasing the rate of increase in the decimation ratio and the rate of reduction in the number of scanlines. When a larger weight is assigned to the image quality than the frame rate, the image transmission device may suppress a reduction in the number of samples per length while maintaining the rate of increase in the decimation ratio and the rate or reduction in the number of scanlines.

In step S1620, the image reception device decodes the compressed data received in step S1610 to reconstruct the first medical image.

In step S1630, the image reception device post-processes the first medical image reconstructed in step S1620 to generate a second medical image. The process of generating the second medical image is performed subsequent to medical image processing performed in the process of generating the first medical image according to the signal path to post-process the first medical image. The post-processing includes at least digital scan conversion and image output and may optionally include 2D filtering or edge emphasis.

Meanwhile, embodiments of the present invention may be implemented as code that can be written in a computer-readable recording medium and thus read by a computer. The computer-readable recording medium may be any type of recording device in which data that can be read by the computer system is stored.

Examples of the computer-readable recording medium include a ROM, a RAM, a CD-ROM, a magnetic tape, a floppy disk, optical data storage, and the like. The computer-readable recording medium can be distributed over computer systems connected to a network so that computer-readable code is written thereto and executed therefrom in a decentralized manner. Functional programs, code, and code segments to realize the embodiments herein can be construed by one of ordinary skill in the art.

While the present invention has been particularly shown and described with reference to exemplary embodiments thereof, those skilled in the art will appreciate that the present invention may be embodied in other specific forms than those set forth herein without departing from the spirit and essential characteristics of the present invention. The above detailed description is therefore to be construed in all aspects as illustrative and not restrictive. The scope of the invention should be determined by reasonable interpretation of the appended claims and all changes coming within the equivalency range of the invention are within the scope of the invention.

INDUSTRIAL APPLICABILITY

According to the above-described first embodiments of the present invention, a data rate of data to be wirelessly transmitted can be adaptively changed by varying signal processing steps performed in a transmitting end and a receiving end according to communication conditions to provide ultrasound images of a uniform frame rate to a user irrespective of communication conditions. In addition, when communication conditions deteriorate and thus an appointed frame rate and image quality cannot be provided, the system can be used with a decimation ratio and the number of scanlines which are changed in consideration of weights designated by a user. Furthermore, battery use of the transmitting end and the receiving end can be efficiently distributed to extend system available time.

According to the above-described second embodiments of the present invention, a medical image acquired by means of a probe is segmented into regions, an ROI of a user is provided with high image quality, and image quality of regions other than the ROI is reduced to minimize the amount of data to be wirelessly transmitted. Accordingly, it is possible to maintain information of interest obtained by the user while minimizing loss of important medical data in a wireless communication network with a limited bandwidth and to supplement an insufficient communication bandwidth by adopting a gradual data reduction method, thereby maximizing user experience.

According to the above-described third embodiments of the present invention, ultrasound images with high quality can be provided through a differential compression and transmission technique according to communication and power conditions in a low interference situation, whereas user experience can be optimized by maintaining a frame rate while reducing the amount of information of images in a situation in which wireless communication interference occurs or residual power is insufficient.

The invention claimed is:

1. A medical image transmission method performed by an image transmission device, comprising:
   acquiring medical image data using a probe;
   generating an evaluation result based on evaluating at least one of a communication state and a power state of a communication medium between the image transmission device and an image reception device;
   determining a reconstruction parameter according to the evaluation result and reconstructing a first medical image from the medical image data according to the reconstruction parameter;
   encoding the reconstructed first medical image to generate compressed data, wherein the generating of the compressed data comprises:
      segmenting the first medical image into at lease two regions; and
      applying a differential image data reduction technique to the segmented regions to generate compressed image data per segmented region, wherein the generating of the reduced image data comprises applying different image data reduction techniques to the segmented regions such that segmented regions other than a region set as a region of interest (ROI) have higher data compressibility in proportion to distance from the ROI; and
   transmitting the generated compressed data to the image reception device to induce the image reception device to generate a post-processed second medical image from the compressed data.

2. The medical image transmission method according to claim 1, wherein the reconstructing of the first medical image comprises variably determining a reconstruction parameter for image reconstruction such that the size of the first medical image is proportional to throughput according to the communication state or residual power according to the power state.

3. The medical image transmission method according to claim 1, wherein the generating of the compressed data comprises:
   determining a data rate necessary for data transmission according to the evaluation result; and
   generating compressed data by selecting a signal path satisfying the determined data rate, wherein the generating of the compressed data comprises variably determining the data rate in proportion to throughput according to the communication state or residual power according to the power state to induce compressed data corresponding to a preset frame rate and image quality to be transmitted to the image reception device.

4. The medical image transmission method according to claim 1, wherein the reconstruction parameter includes at least one of a dynamic range, a contrast, a gain, an amplitude threshold, an image sharpness and a resolution.

5. A medical image transmission method performed by an image transmission device, comprising:
   acquiring medical image data using a probe;
   generating an evaluation result based on evaluating at least one of a communication state and a power state of a communication medium between the image transmission device and an image reception device;
   determining a reconstruction parameter according to the evaluation result and reconstructing a first medical image from the medical image data according to the reconstruction parameter;
   determining a data rate necessary for data transmission according to the evaluation result;
   encoding the reconstructed first medical image to generate compressed data by selecting a signal path satisfying the determined data rate, wherein the generating of the compressed data comprises variably determining the data rate in proportion to throughput according to the communication state or residual power according to the power state to induce compressed data corresponding to a preset frame rate and image quality to be transmitted to the image reception device; and
   transmitting the generated compressed data to the image reception device to induce the image reception device to generate a post-processed second medical image from the compressed data.

6. The medical image transmission method according to claim 5, wherein the generating of the compressed data comprises: segmenting the first medical image into at least two regions; and applying a differential image data reduction technique to the segmented regions to generate compressed image data per segmented region, wherein the generating of the reduced image data comprises applying different image data reduction techniques to the segmented regions such that segmented regions other than a region set as a region of interest (ROI) have higher data compressibility in proportion to distance from the ROI.

* * * * *